United States Patent
Nakamura et al.

(10) Patent No.: US 11,805,986 B2
(45) Date of Patent: Nov. 7, 2023

(54) FLEXIBLE TUBE INSERTION APPARATUS, STIFFNESS CONTROL APPARATUS, INSERTION METHOD, AND RECORDING MEDIUM STORING STIFFNESS CONTROL PROGRAM

(71) Applicant: OLYMPUS CORPORATION, Tokyo (JP)

(72) Inventors: Shuji Nakamura, Akishima (JP);
Takeshi Takahashi, Hachioji (JP);
Yuichi Ikeda, Tama (JP)

(73) Assignee: OLYMPUS CORPORATION, Tokyo (JP)

( * ) Notice: Subject to any disclaimer, the term of this patent is extended or adjusted under 35 U.S.C. 154(b) by 470 days.

(21) Appl. No.: 17/005,973

(22) Filed: Aug. 28, 2020

(65) Prior Publication Data

US 2020/0390315 A1 Dec. 17, 2020

Related U.S. Application Data

(63) Continuation of application No. PCT/JP2018/008587, filed on Mar. 6, 2018.

(51) Int. Cl.
*A61B 1/005* (2006.01)
*A61B 1/00* (2006.01)
*A61B 1/06* (2006.01)

(52) U.S. Cl.
CPC ........ *A61B 1/0057* (2013.01); *A61B 1/00078* (2013.01); *A61B 1/0684* (2013.01); *A61B 2562/02* (2013.01)

(58) Field of Classification Search
CPC . A61B 1/00071; A61B 1/00078; A61B 1/005; A61B 1/051; A61B 1/0052;
(Continued)

(56) References Cited

U.S. PATENT DOCUMENTS 5,482,029 A 1/1996 Sekiguchi et al.
5,885,208 A 3/1999 Moriyama
(Continued)

FOREIGN PATENT DOCUMENTS

JP 6-70879 A1 3/1994
JP 6-181882 A1 7/1994
(Continued)

OTHER PUBLICATIONS

Japanese Office Action dated Sep. 21, 2021 received in 2020-504532.
(Continued)

*Primary Examiner* — Ryan N Henderson
(74) *Attorney, Agent, or Firm* — Scully, Scott, Murphy & Presser, P.C.

(57) ABSTRACT

A flexible tube insertion apparatus includes a flexible insertion section to be inserted into a subject and bent by a reaction force from the subject, a variable stiffness unit provided in the insertion section and configured to change a stiffness of the insertion section, and a shape detector configured to detect a bent shape of the insertion section. The apparatus further includes a force specifier configured to acquire a distribution of the reaction force on a distal side from a predetermined point in the bent shape and specify a maximum reaction force position, and a stiffness controller configured to control a stiffness of the variable stiffness unit so as to increase a stiffness of the variable stiffness unit between the predetermined point and the maximum reaction force position.

9 Claims, 20 Drawing Sheets

(58) Field of Classification Search
CPC ... A61B 1/0053; A61B 1/0055; A61B 1/0056; A61B 1/0057; A61B 1/0058; A61B 1/008; A61B 1/0051; A61B 34/30; A61B 2034/303

See application file for complete search history.

(56) References Cited

U.S. PATENT DOCUMENTS

| | | | | |
|---|---|---|---|---|
| 10,349,819 | B2* | 7/2019 | Ikeda | A61B 1/00006 |
| 10,694,926 | B2* | 6/2020 | Ikeda | A61B 1/0055 |
| 10,959,604 | B2* | 3/2021 | Ikeda | A61B 1/00163 |
| 11,317,790 | B2* | 5/2022 | Nakamura | A61B 1/00006 |
| 11,344,376 | B2* | 5/2022 | Diolaiti | A61M 25/0147 |
| 2013/0178705 | A1* | 7/2013 | Takeuchi | G02B 23/2476 600/144 |
| 2014/0230562 | A1 | 8/2014 | Yamamoto et al. | |
| 2017/0055809 | A1 | 3/2017 | Omoto et al. | |
| 2017/0079508 | A1* | 3/2017 | Ikeda | A61B 1/00006 |
| 2017/0321666 | A1* | 11/2017 | Morishima | A61B 1/00078 |
| 2018/0028049 | A1* | 2/2018 | Takahashi | A61B 1/0057 |
| 2018/0064310 | A1* | 3/2018 | Takahashi | A61B 1/0055 |
| 2018/0078118 | A1* | 3/2018 | Takahashi | A61B 1/00009 |
| 2018/0078122 | A1* | 3/2018 | Ikeda | A61B 1/0055 |
| 2018/0263467 | A1* | 9/2018 | Takahashi | A61B 1/00045 |
| 2018/0263468 | A1* | 9/2018 | Morishima | A61B 1/0058 |
| 2018/0266402 | A1* | 9/2018 | Takahashi | F03G 7/065 |
| 2018/0303313 | A1* | 10/2018 | Nakamura | A61B 1/009 |
| 2018/0303319 | A1* | 10/2018 | Ikeda | A61B 1/0051 |
| 2019/0046010 | A1* | 2/2019 | Tojo | A61B 1/0058 |
| 2019/0046011 | A1* | 2/2019 | Ikeda | A61B 1/0051 |
| 2019/0046012 | A1* | 2/2019 | Ikeda | A61B 1/00066 |
| 2019/0082933 | A1* | 3/2019 | Takahashi | A61B 1/0051 |
| 2019/0082935 | A1* | 3/2019 | Kitanaka | A61M 25/0102 |
| 2019/0099064 | A1* | 4/2019 | Nakamura | A61B 1/00147 |
| 2019/0231449 | A1* | 8/2019 | Diolaiti | A61B 1/0016 |
| 2019/0248031 | A1* | 8/2019 | Takahashi | G02B 23/24 |
| 2019/0374089 | A1* | 12/2019 | Nakamura | A61B 1/009 |
| 2020/0037852 | A1* | 2/2020 | Takahashi | A61B 1/0055 |
| 2020/0037853 | A1* | 2/2020 | Kitanaka | A61B 1/00078 |
| 2020/0046204 | A1* | 2/2020 | Morishima | A61B 1/00114 |
| 2020/0257105 | A1* | 8/2020 | Okita | A61B 1/00078 |
| 2020/0367724 | A1* | 11/2020 | Takahashi | A61B 1/00006 |
| 2020/0390315 | A1* | 12/2020 | Nakamura | G02B 23/24 |
| 2021/0000329 | A1* | 1/2021 | Tezuka | A61B 1/00006 |
| 2021/0048355 | A1* | 2/2021 | Hane | G01D 5/20 |
| 2021/0369084 | A1* | 12/2021 | Nakamura | A61B 1/00078 |
| 2021/0378485 | A1* | 12/2021 | Kugo | A61B 1/00078 |
| 2022/0296079 | A1* | 9/2022 | Takahashi | A61B 1/005 |

FOREIGN PATENT DOCUMENTS

| | | |
|---|---|---|
| JP | 10-314106 A1 | 12/1998 |
| JP | 2013-94337 A1 | 5/2013 |
| JP | 2016-7434 A | 1/2016 |
| WO | 2016/063682 A1 | 4/2016 |
| WO | 2016/151846 A1 | 9/2016 |

OTHER PUBLICATIONS

English translation of International Preliminary Report on Patentability dated Sep. 17, 2020, together with the Written Opinion issued in International Application No. PCT/JP2018/008587.

International Search Report dated May 15, 2018 received in PCT/JP2018/008587.

* cited by examiner

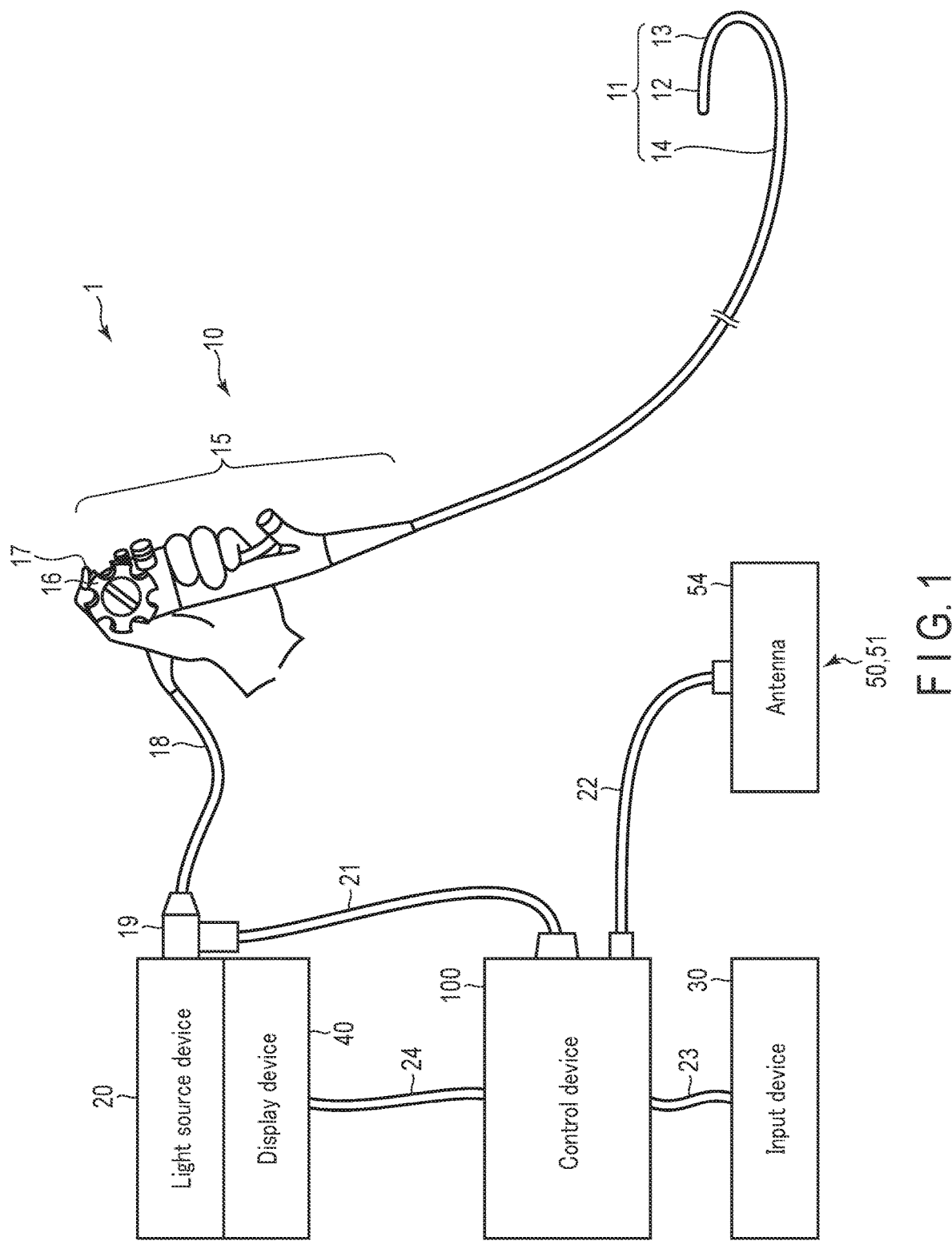
F I G. 1

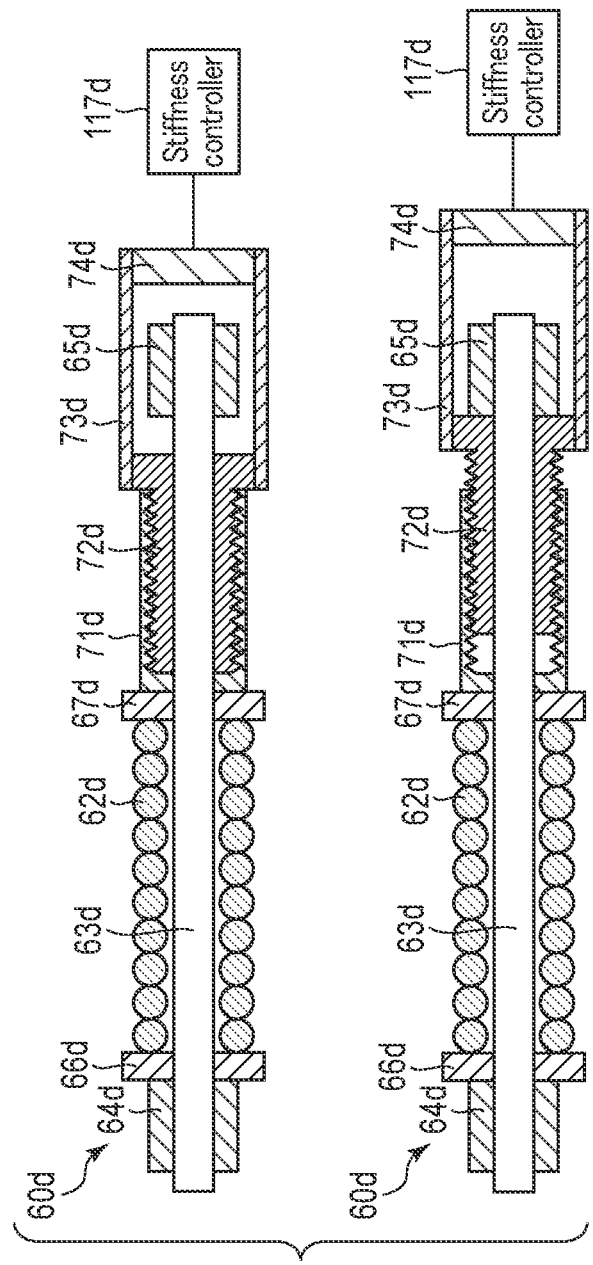
F I G. 9

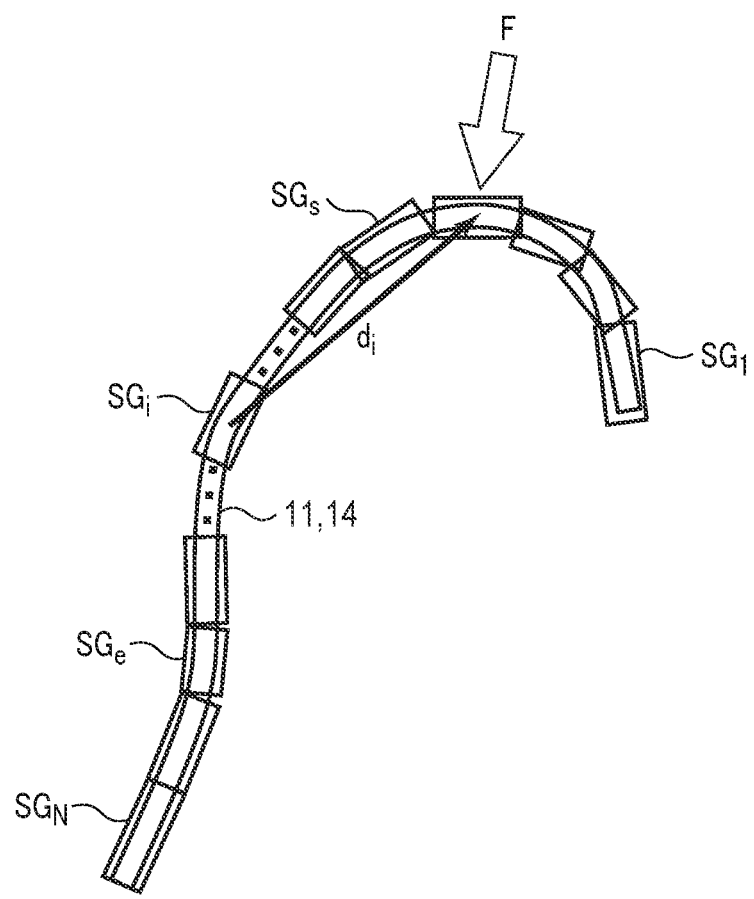
F I G. 24

FLEXIBLE TUBE INSERTION APPARATUS, STIFFNESS CONTROL APPARATUS, INSERTION METHOD, AND RECORDING MEDIUM STORING STIFFNESS CONTROL PROGRAM

CROSS-REFERENCE TO RELATED APPLICATIONS

This application is a Continuation Application of PCT Application No. PCT/JP2018/008587, filed Mar. 6, 2018, the entire contents of which are incorporated herein by reference.

BACKGROUND OF THE INVENTION

1. Field of the Invention

The present invention relates to a flexible tube insertion apparatus including a flexible tube section to be inserted into a subject, a stiffness control apparatus, an insertion method, and a recording medium storing a stiffness control program.

2. Description of the Related Art

A flexible tube insertion apparatus, such as an endoscope apparatus, with the bending stiffness of its insertion section (flexible tube section) partly changed in order to improve the insertability of the insertion section, is known.

For example, Jpn. Pat. Appln. KOKAI Publication No. H6-70879 discloses an endoscope apparatus in which segments are set in an insertion section so that the flexibility of the insertion section can be controlled for each segment. In this endoscope apparatus, the flexibility of each segment is changed using shape information of the endoscope and a database storing flexibility patterns based on past insertion into a subject.

For example, Jpn. Pat. Appln. KOKAI Publication No. 2016-7434 discloses an endoscope apparatus in which an insertion section is divided into segments in the longitudinal direction, a bent shape of each segment is detected, and the bending stiffness of each segment is varied according to the detected bent shape.

For example, International Publication No. 2016/151846 discloses a flexible tube insertion apparatus in which the bending stiffness of an insertion section is varied according to the insertion state, for example, the bending state of the insertion section.

BRIEF SUMMARY OF THE INVENTION

An aspect of the invention is directed to a flexible tube insertion apparatus. The flexible tube insertion apparatus includes: a flexible insertion section having a distal end and a proximal end, configured to be inserted into a subject from the distal end, and further configured to bend by receiving a reaction force from the subject when the insertion section comes into contact with the subject; a variable stiffness unit provided at least partially in the insertion section and configured to change a stiffness of the insertion section in a position where the variable stiffness unit is provided; a shape detector configured to detect a bent shape of the insertion section; a reaction force value specifier configured to acquire a distribution of values of the reaction force on a distal side from a predetermined point in the bent shape and specify a maximum reaction force position at which the value of the reaction force is at a maximum; and a stiffness controller configured to control a stiffness of the variable stiffness unit so as to increase a stiffness of the variable stiffness unit positioned between the predetermined point and the maximum reaction force position.

An aspect of the invention is directed to a stiffness control apparatus configured to control a stiffness of a variable stiffness unit. The variable stiffness unit is provided at least partially in a flexible insertion section and configured to change a stiffness of the insertion section in a position where the variable stiffness unit is provided. The insertion section has a distal end and a proximal end, and is configured to be inserted into a subject from the distal end, and further configured to bend by receiving a reaction force from the subject when the insertion section comes into contact with the subject. The stiffness control apparatus includes: a reaction force value specifier configured to acquire a bent shape of the insertion section, acquire a distribution of values of the reaction force on a distal side from a predetermined point in the bent shape, and specify a maximum reaction force position at which the value of the reaction force is at a maximum; and a stiffness controller configured to control a stiffness of the variable stiffness unit so as to increase a stiffness of the variable stiffness unit positioned between the predetermined point and the maximum reaction force position.

An aspect of the invention is directed to an insertion method of a flexible insertion section. The flexible insertion section has a distal end and a proximal end, and is configured to be inserted into a subject from the distal end, and further configured to bend by receiving a reaction force from the subject when the insertion section comes into contact with the subject. The method includes: acquiring a bent shape of the insertion section, acquiring a distribution of values of the reaction force on a distal side from a predetermined point in the bent shape, and specifying a maximum reaction force position at which the value of the reaction force is at a maximum; and increasing a stiffness of a variable stiffness unit positioned between the predetermined point and the maximum reaction force position, the variable stiffness unit being provided at least partially in the insertion section and configured to change a stiffness of the insertion section in a position where the variable stiffness unit is provided.

An aspect of the invention is directed to a computer-readable recording medium storing a stiffness control program. The stiffness control program is configured to cause a computer to function as: a reaction force value specifier configured to acquire a bent shape of a flexible insertion section, acquire a distribution of values of the reaction force on a distal side from a predetermined point in the bent shape, and specify a maximum reaction force position at which the value of the reaction force is at a maximum, the insertion section having a distal end and a proximal end, configured to be inserted into a subject from the distal end, and further configured to bend by receiving a reaction force from the subject when the insertion section comes into contact with the subject; and a stiffness controller configured to control a stiffness of a variable stiffness unit so as to increase a stiffness of the variable stiffness unit when the variable stiffness unit is positioned between the predetermined point and the maximum reaction force position; the variable stiffness unit provided at least partially in the insertion section and configured to change a stiffness of the insertion section in a position where the variable stiffness unit is provided.

Advantages of the invention will be set forth in the description that follows, and in part will be obvious from the description, or may be learned by practice of the invention.

The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic diagram showing an example of an endoscope apparatus according to a first embodiment.

FIG. 9 is a schematic diagram showing an example of a variable stiffness unit that adopts a mechanism related to core wire tensile stress.

FIG. 24 is a diagram showing an example of a pressing force F applied to the insertion section and a vector $d_i$ extending from the center of the segment $SG_i$ to the position to which the pressing force F is applied.

DETAILED DESCRIPTION OF THE INVENTION

Figure 2:
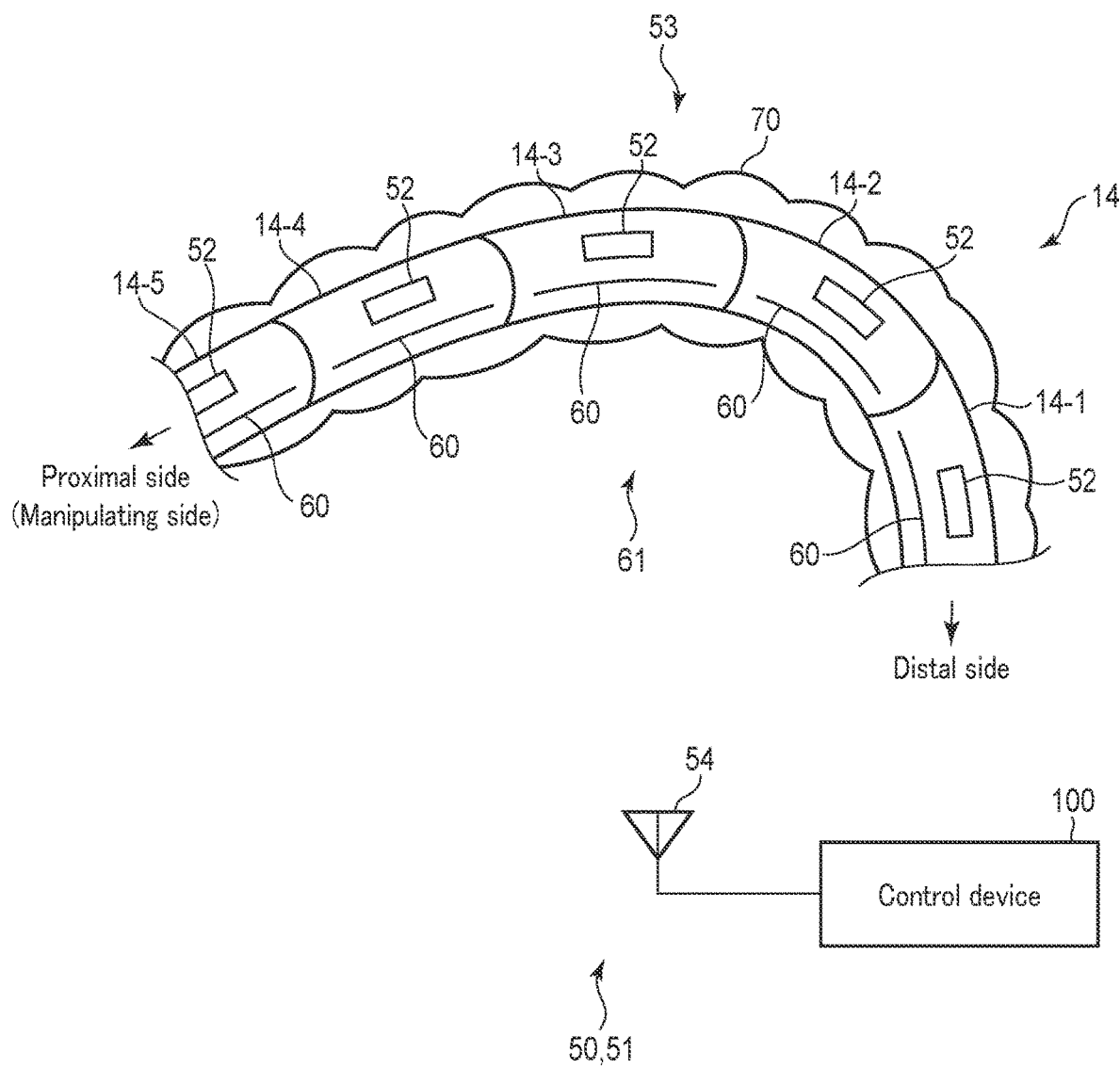
FIG. 2 is a diagram showing an example of a flexible tube section of the endoscope apparatus including a bent shape detection device.

Hereinafter, embodiments of the present invention will be described with reference to the accompanying drawings. An endoscope apparatus will be described below as an example of a flexible tube insertion apparatus of the present invention.

First Embodiment (Configuration of Endoscope Apparatus)

FIG. 1 is a schematic diagram showing an example of an endoscope apparatus 1 according to a first embodiment. The endoscope apparatus 1 includes an endoscope 10, a light source device 20, an input device 30, a display device 40, a shape detection device 50, and a control device 100.

The endoscope 10 includes a tubular insertion section 11 to be inserted into a subject, and a control section 15 provided on a proximal side of the insertion section 11. The insertion section 11 includes a distal end hard section 12, a bendable section 13, and a flexible tube section 14 arranged in the mentioned order from the distal side to the proximal side. The distal end hard section 12 incorporates therein, for example, an optical system for illumination and an optical system for observation (not shown), as well as an imaging element 25 shown in FIG. 3. The bendable section 13 is a portion that is bent in accordance with the operation of the control section 15. The bendable section 13 is connected to the distal side of the flexible tube section 14. The flexible tube section 14 is a flexible, elongated tubular portion. The control section 15 is provided with an angle knob 16. When a surgeon manipulates the angle knob 16, the bendable section 13 is bent in any direction. That is, the bendable section 13 can actively change its bending shape. In addition, the control section 15 is provided with one or more switches 17, to which functions, such as freezing and recording of endoscopic images and focus switching, are assigned by the setting of the control device 100.

Since the distal end hard section 12 is a very short portion and the bendable section 13 is bendable in the insertion section 11, the term "flexible tube" used herein refers not only to the flexible tube section 14 but also to the entire insertion section 11. For example, the endoscope apparatus 1 as a flexible tube insertion apparatus includes the insertion section 11 as a flexible tube. The insertion section 11 has a distal end and a proximal end, and is inserted into a subject from the distal end. The insertion section 11 is bent upon receiving a reaction force from the subject when brought into contact with the subject.

The shape detection device 50 is configured to detect the shape of the insertion section 11, for example, the shape of the flexible tube section 14. FIG. 2 shows a magnetic shape sensor 51 as an example of a shape detector constituting the shape detection device 50.

FIG. 2 is a schematic diagram showing an example of the flexible tube section 14 of the endoscope apparatus 1 including the shape sensor 51. The flexible tube section 14 shown in FIG. 2 is in a state of being inserted into a bent subject 70. The shape sensor 51 includes a source coil array 53, including source coils 52, for detection of the shape of the flexible tube section 14. The source coil 52 is a magnetic field-generating element configured to generate a magnetic field.

The source coils 52 in the source coil array 53 are arranged at intervals in the longitudinal direction, that is, the axial direction of the flexible tube section 14. For convenience, it is assumed that the flexible tube section 14 is formed of one or more segments aligned in the axial direction of the flexible tube section 14. Herein, the segment refers to a virtual unit that equally divides the flexible tube section 14 in the longitudinal direction. That is, it is assumed that the flexible tube section 14 is divided into segments along the axial direction from the distal side to the proximal side. For example, FIG. 2 shows five segments 14-1, 14-2, 14-3, 14-4, and 14-5 aligned along the axial direction from the distal side to the proximal side, and each of the segments is provided with one source coil 52. The arrangement of the source coils 52 is not limited to this example, and the source coils may be arranged only in some of the segments.

The shape sensor 51 includes an antenna 54 for detecting a magnetic field generated by the source coil 52. The antenna 54 is provided separately from the endoscope 10, and is disposed around a subject into which the endoscope 10 is inserted. The antenna 54 is connected to the control device 100. The connection between the antenna 54 and the control device 100 may be by wire or wirelessly.

Although FIG. 2 shows a configuration in which the source coils 52 are preinstalled in the flexible tube section 14, a probe incorporating source coils may be inserted into a channel extending in the longitudinal direction in the insertion section 11.

Referring back to FIG. 1, the light source device 20 is connected to the endoscope 10 through a cable connector 19 at the distal end of a universal cable 18 extending from the control section 15. The universal cable 18 includes a light guide connected to the aforementioned optical system for illumination, a transmission cable connected to the imaging element 25, and the like. The light source device 20 includes a general light emitting element such as a laser diode (LD) or a light emitting diode (LED). The light source device 20 supplies illumination light to be emitted from an illumination window of the distal end hard section 12 through the light guide.

Figure 3:
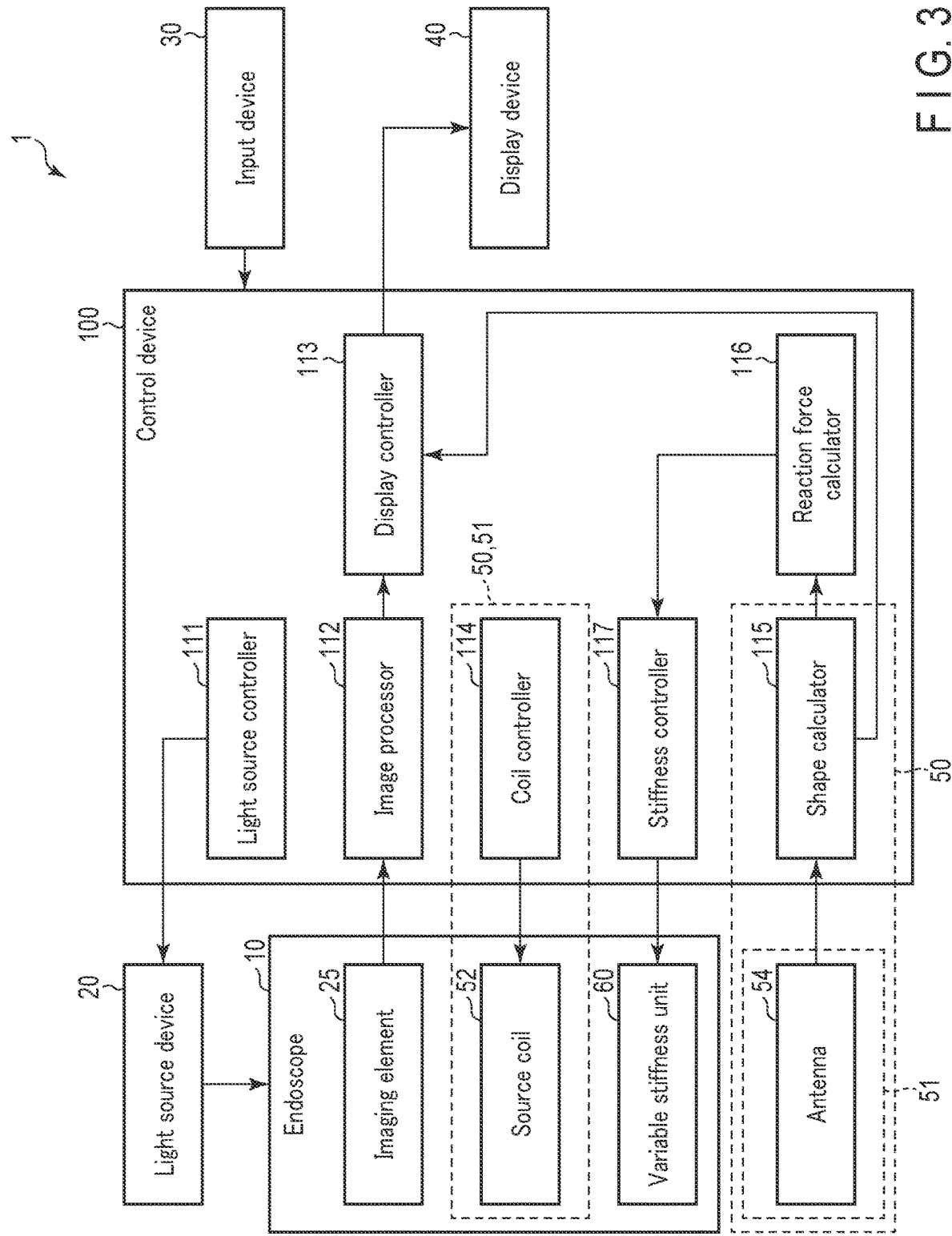
FIG. 3 is a block diagram showing an example of the endoscope apparatus according to the first embodiment.

FIG. 3 is a block diagram showing an example of the endoscope apparatus 1 according to the first embodiment. The control device 100 includes a light source controller 111, an image processor 112, a display controller 113, a coil controller 114, a shape calculator 115, a reaction force calculator 116, and a stiffness controller 117. As shown in FIG. 1, the control device 100 is connected to the endoscope 10 and the light source device 20 through the cable connector 19 and a cable 21. The control device 100 is also connected to the antenna 54 through a cable 22.

Each of the above-described elements of the control device 100 may be composed of a processor such as a CPU. In this case, various programs for causing the processor to function as these elements are, for example, prepared in an internal memory or an external memory (not shown), and the processor executes the programs to implement functions of the elements of the control device 100. Alternatively, each of the elements of the control device 100 may be composed of a hardware circuit such as an application specific integrated circuit (ASIC), a field-programmable gate array (FPGA), or the like.

The above-described elements of the control device 100, in particular, the shape calculator 115, the reaction force calculator 116, and the stiffness controller 117, may be included in a control device separately from the control device 100. For example, the shape calculator 115, the reaction force calculator 116, and the stiffness controller 117 may be included in a control device separately from an endoscopic video image processor including the light source controller 111 and the image processor 112. Alternatively, the shape calculator 115, the reaction force calculator 116, and the stiffness controller 117 may be included in different control devices. That is, the processors or hardware circuits that function as the aforementioned elements of the control device 100, in particular, the shape calculator 115, the reaction force calculator 116, and the stiffness controller 117, may be included in either a single housing or multiple housings, as long as the functions of the aforementioned elements can be implemented.

The light source controller 111 performs, for example, dimming control of the illumination light of the light source device 20. The image processor 112 converts an electric signal obtained by converting light from an object by the imaging element 25 of the endoscope 10 into a video signal. The display controller 113 controls the operation of the display device 40.

The coil controller 114 includes a coil output section configured to output a voltage to be applied to each source coil 52 of the source coil array 53, and controls the voltage to be applied from the coil output section to the source coils 52.

The shape calculator 115 calculates the coordinates of the position of each source coil 52 based on the detection signal of the magnetic field of each source coil 52 received by the antenna 54. That is, the shape calculator 115 calculates the shape of the insertion section 11, for example, the shape of the flexible tube section 14, based on the state information acquired from each source coil 52 and the antenna 54 as a shape detector. Also, the shape calculator 115 specifies an apex of a bent shape, for example, a position of a flexure point in the calculated shape, as will be described later. That is, the shape calculator 115 functions as an apex specifier configured to specify the apex of the bent shape of the flexible tube section 14. The shape calculator 115 includes a receiver configured to receive a detection signal from the antenna 54.

The reaction force calculator 116 acquires the shape calculated by the shape calculator 115 and a current stiffness value of a variable stiffness unit 60 described later. The reaction force calculator 116 calculates a value of a reaction force that the flexible tube section 14 receives from the subject 70 based on the acquired shape and current stiffness value. For example, the reaction force calculator 116 functions as a reaction force value specifier configured to calculate and thereby acquire a distribution of the reaction force value along the longitudinal direction of the flexible tube section 14, on the distal side from the apex in the bent shape calculated by the shape calculator 115, and specify a maximum reaction force position at which the calculated reaction force value is at a maximum, as will be described later.

The stiffness controller 117 includes a variable stiffness output section configured to output a voltage to be applied to the variable stiffness unit 60 described later, and control the voltage to be applied from the variable stiffness output section to the variable stiffness unit 60. The stiffness controller 117 includes, for example, a storage (not shown). The storage stores, for example, the current stiffness value of the variable stiffness unit 60. When the stiffness of the variable stiffness unit 60 is changed, the current stiffness value is updated.

In the present embodiment, the source coils 52 of the source coil array 53, the antenna 54, and the coil controller 114 and the shape calculator 115 of the control device 100 constitute the shape detection device 50. In order to support the insertion of the insertion section 11 of the endoscope 10, the shape detection device 50 receives the magnetic fields generated by the source coils 52 of the source coil array 53, with the antenna 54, to detect position information or shape information of the flexible tube section 14, and calculates the shape of the flexible tube section 14 at the shape calculator 115 based on the detected information.

The shape detection device 50 is not limited to this. The shape detection device 50 is discretionary as long as it can detect the shape of the insertion section 11, for example, the shape of the flexible tube section 14, and may be configured by any one of the following: sensing that utilizes changes in a quantity or an optical property of light that propagates through a light guide, such as an optical fiber (fiber sensor); sensing that utilizes electromagnetic waves (electromagnetic sensor); sensing that utilizes ultrasonic waves (ultrasonic sensor); sensing that utilizes distortion (distortion sensor); and sensing that utilizes an X-ray absorbing material, or a combination thereof.

Next, the variable stiffness unit 60 will be described. As shown in FIG. 2, the flexible tube section 14 is provided with a variable stiffness unit array 61 including at least one variable stiffness unit 60. The variable stiffness units 60 vary the bending stiffness of the flexible tube section 14 in units of segments, each segment including a variable stiffness unit 60. The variable stiffness unit 60 can vary the bending stiffness of the corresponding segment within a range from a predetermined minimum value up to a predetermined maximum value. The number of variable stiffness units 60 is not particularly limited. One or more variable stiffness units 60 may be provided at least partially in the flexible tube section 14.

Figure 4:
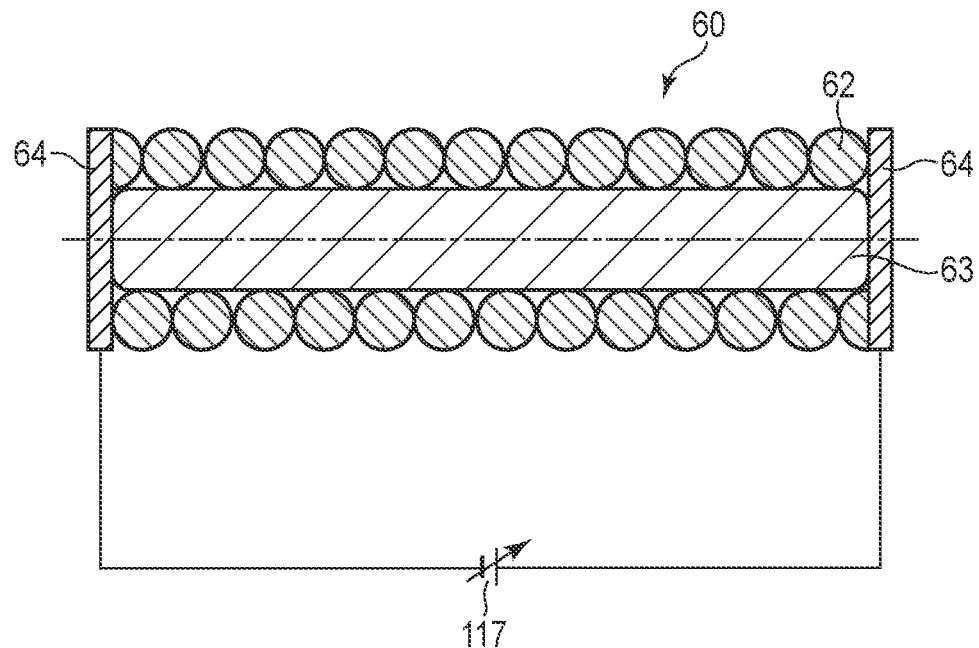
FIG. 4 is a schematic diagram showing an example of a variable stiffness unit that adopts an artificial muscle.

FIG. 4 is a schematic diagram showing an example of the variable stiffness unit 60. The variable stiffness unit 60 includes a coil pipe 62 made of a metal wire, an electroactive polymer artificial muscle (EPAM) 63 contained inside the coil pipe 62, and electrodes 64 provided at both ends of the coil pipe 62. The voltage output from the stiffness controller 117 is applied across the EPAM 63 inside the coil pipe 62 through the electrodes 64. The EPAM 63 is an actuator configured to expand and contract under application of a voltage, so as to vary the hardness. Each of the variable stiffness units 60 is incorporated in the flexible tube section 14 so that the central axis of the coil pipe 62 is coincident with or parallel to the central axis of the flexible tube section 14. The EPAM 63 of each variable stiffness unit 60 has a stiffness greater than that of a member constituting the flexible tube section 14, such as fluororesin.

Figure 5:
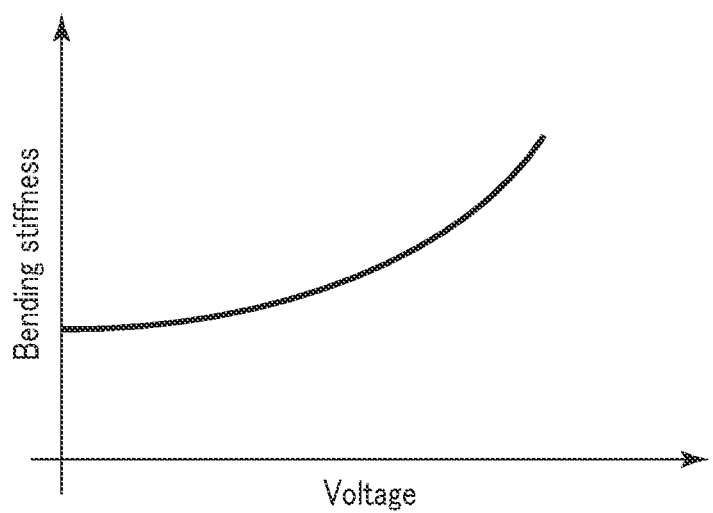
FIG. 5 is a diagram showing an example of voltage versus bending stiffness of the variable stiffness unit shown in FIG. 4.

When the stiffness controller 117 outputs a voltage from its variable stiffness output section, the voltage is applied to the electrodes 64 and the EPAM 63 of each variable stiffness unit 60. When the voltage is applied, the EPAM 63 tends to increase its diameter about the central axis of the coil pipe 62. With the EPAM 63 contained inside the coil pipe 62, however, the increase of the diameter is hampered. As a result, the variable stiffness unit 60 exhibits a higher bending stiffness value as the value of the applied voltage increases, as shown in FIG. 5. That is, in accordance with the variation in the hardness of the variable stiffness unit 60, the bending stiffness of the flexible tube section 14 incorporating the variable stiffness unit 60 also varies.

As described above, the endoscope apparatus 1 has a variable stiffness function to change the bending stiffness of the flexible tube section 14 through application of a voltage to the variable stiffness units 60 by the stiffness controller 117. The stiffness controller 117 controls the voltages to be applied to the variable stiffness units 60 separately, so that the bending stiffness of the segments of the flexible tube section 14 is independently varied. That is, different bending stiffness values can be set for each segment of the flexible tube section 14.

Although a variable stiffness unit that adopts an artificial muscle is described above as an example of the variable stiffness unit 60, the variable stiffness unit 60 is not limited thereto. Various mechanisms can be adopted for the variable stiffness unit for varying the bending stiffness of the flexible tube section 14, examples of which include a variable stiffness unit that adopts a shape-memory member, a variable stiffness unit that adopts a so-called joint lock mechanism, a variable stiffness unit that adopts a hybrid mechanism of a joint lock mechanism and a shape-memory member, and a variable stiffness unit that adopts a mechanism related to a core wire tensile stress. These various mechanisms will be described below with reference to FIGS. 6 to 9.

Figure 6:
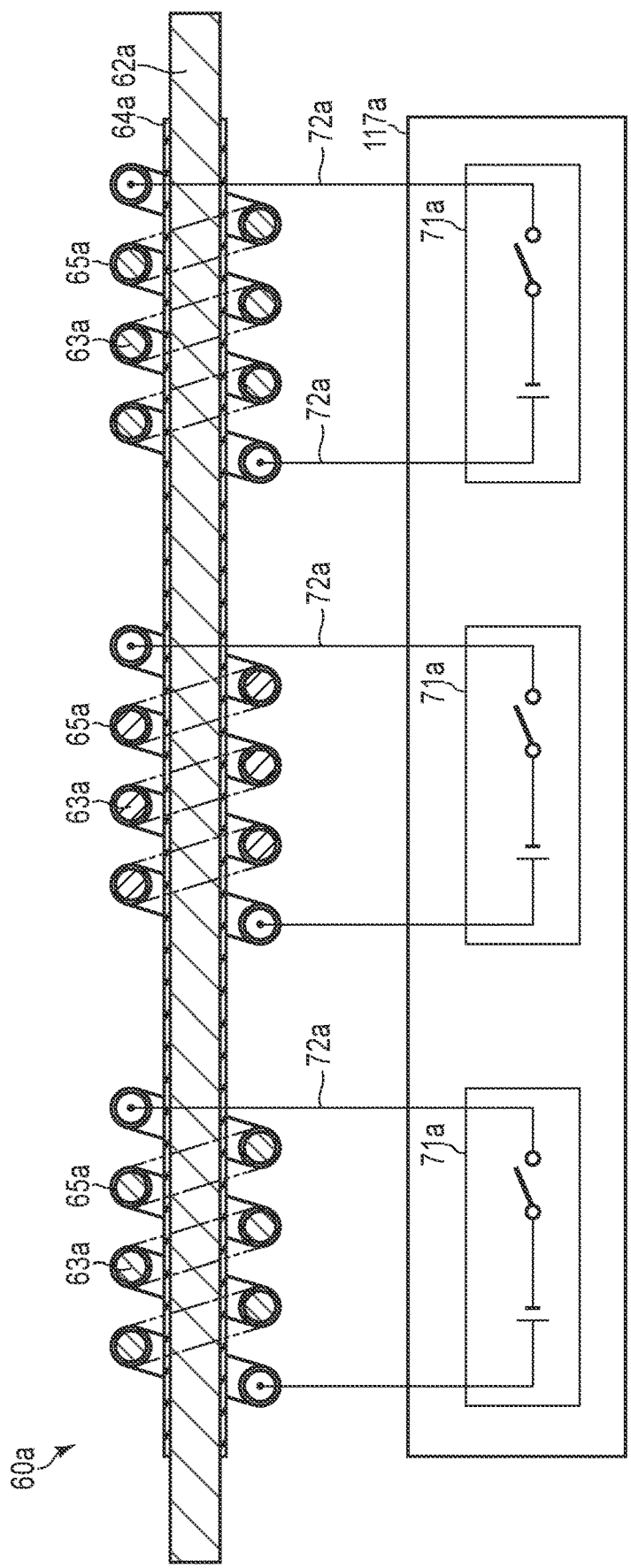
FIG. 6 is a schematic diagram showing an example of a variable stiffness unit that adopts a shape-memory member.

FIG. 6 is a schematic diagram showing an example of a variable stiffness unit 60a that adopts a shape-memory member. The variable stiffness unit 60a includes an elongated shape-memory member 62a and at least one induction member 63a arranged around the shape-memory member 62a. FIG. 6 shows three coiled induction members 63a. The shape-memory member 62a may be made of a shape-memory alloy such as a NiTi-containing alloy. An insulation film 64a for preventing a short circuit between the shape-memory member 62a and the induction member 63a is provided on the outer surface of the shape-memory member 62a. The induction member 63a may be made of a conductive material, and is a member configured to generate heat, such as an electric heating wire. An insulation film 65a, for preventing a short circuit between the shape-memory member 62a and the induction member 63a and between the adjacent induction members 63a, is provided on the outer surface of the induction member 63a.

A stiffness controller 117a includes a drive circuit 71a including a power supply and a switch. The number of drive circuits 71a corresponds to the number of induction members 63a, and the drive circuit 71a is connected to the induction member 63a by wiring 72a. The stiffness controller 117a can switch a current supplied to the induction member 63a both ON and OFF.

The shape-memory member 62a undergoes phase transition, inside and near the induction member 63a, between a first phase in which the shape-memory member 62a is in a soft state and a second phase in which the shape-memory member 62a is in a hard state stored in advance as a current supplied from the stiffness controller 117a to the induction member 63a is switched between ON and OFF. For example, at normal times, that is, when no current is supplied, the shape-memory member 62a assumes the first phase to be in a soft state, and when a current is supplied, the shape-memory member 62a assumes the second phase to be in a hard state.

Each drive circuit 71a of the stiffness controller 117a can independently switch ON and OFF. Therefore, arranging such a variable stiffness unit 60a, which includes the shape-memory member 62a, in the flexible tube section 14 allows varying the bending stiffness of the flexible tube section 14 at a desired position.

Figure 7:
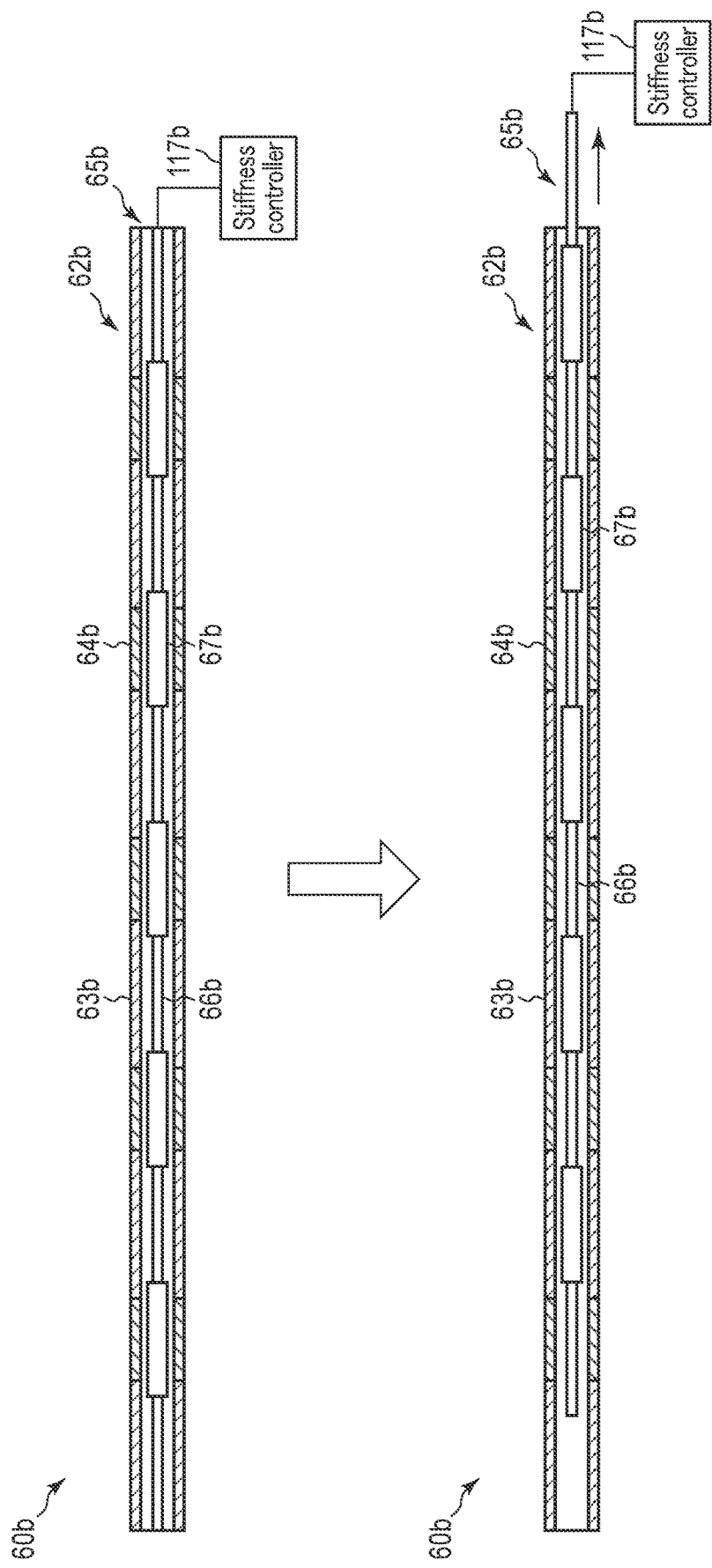
FIG. 7 is a schematic diagram showing an example of a variable stiffness unit that adopts a joint lock mechanism.

FIG. 7 is a schematic diagram showing an example of a variable stiffness unit 60b that adopts a so-called joint lock mechanism. The variable stiffness unit 60b includes an elongated cylindrical first longitudinal member 62b and a second longitudinal member 65b passing slidably through the hollow inner part of the first longitudinal member 62b. The first longitudinal member 62b has first bending stiffness sections 63b having a relatively high bending stiffness value and second bending stiffness sections 64b having a relatively low bending stiffness value, which are alternately located along the longitudinal direction. The second longitudinal member 65b has first sections 66b having a small diameter and relatively easy to bend and second sections 67b having a large diameter and relatively difficult to bend, which are alternately located along the longitudinal direction.

In the variable stiffness unit 60b, a relative positional relationship between the first longitudinal member 62b and the second longitudinal member 65b in the longitudinal direction is changed, so that a state in which the bending stiffness is relatively high and a state in which the bending stiffness is relatively low are switched. For example, in a state where the first bending stiffness section 63b of the first longitudinal member 62b and the first section 66b of the second longitudinal member 65b are aligned in the longitudinal direction, and the second bending stiffness section 64b of the first longitudinal member 62b and the second section 67b of the second longitudinal member 65b are aligned in the longitudinal direction, as shown in the upper part of FIG. 7, the variable stiffness unit 60b is in a hard state where it is difficult to bend. Also, in a state where the second bending stiffness section 64b of the first longitudinal member 62b and the first section 66b of the second longitudinal member 65b are aligned, as shown in the lower part of FIG. 7, the variable stiffness unit 60b is in a soft state where it is easily bent.

A stiffness controller 117b includes a drive unit such as a motor (not shown), and changes the position of the second longitudinal member 65b so as to change the position of the second longitudinal member 65b in the longitudinal direction with respect to the first longitudinal member 62b.

Arranging such a variable stiffness unit 60b in the flexible tube section 14 allows varying the bending stiffness of the flexible tube section 14 at a desired position.

Figure 8:
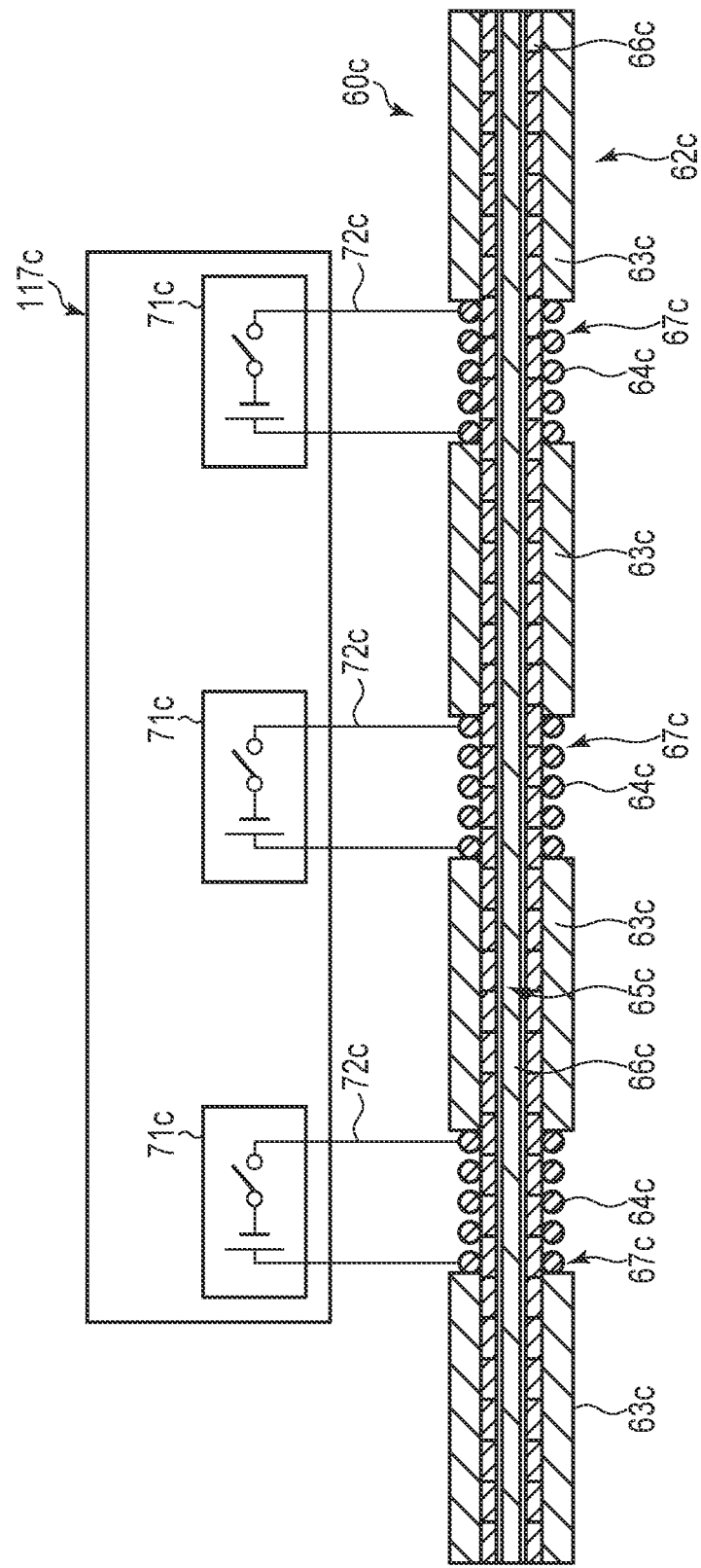
FIG. 8 is a schematic diagram showing an example of a variable stiffness unit formed of a hybrid of a joint lock mechanism and a shape-memory member.

FIG. 8 is a schematic diagram showing an example of a variable stiffness unit 60c formed of a hybrid of a joint lock mechanism and a shape-memory member. The variable stiffness unit 60c includes: an elongated cylindrical first longitudinal member 62c, constituted by alternately arranging first bending stiffness sections 63c having a relatively high bending stiffness value and second bending stiffness sections 64c having a relatively low bending stiffness value in the longitudinal direction; and a second longitudinal member 65c passing slidably through the hollow inner part of the first longitudinal member 62c. For example, the second longitudinal member 65c is formed of a shape-memory member 66c, and may be a shape-memory alloy such as a NiTi-containing alloy.

A stiffness controller 117c includes a drive circuit 71c including a power supply and a switch. The number of drive circuits 71c corresponds to the number of second bending stiffness sections 64c, and the drive circuit 71c is connected to the second bending stiffness section 64c by wiring 72c. The second bending stiffness section 64c functions as an induction member 67c configured to cause the shape-memory member 66c to undergo phase transition between a first phase, in which the shape-memory member 66c is in a soft state, and a second phase, in which the shape-memory member 66c is in a hard state stored in advance, by the switching ON and OFF of a current supplied from the stiffness controller 117c.

Arranging such a variable stiffness unit 60c formed of a hybrid of a joint lock mechanism and a shape-memory member in the flexible tube section 14 also allows varying the bending stiffness of the flexible tube section 14 at a desired position.

FIG. 9 is a schematic diagram showing an example of a variable stiffness unit 60d that adopts a mechanism related to core wire tensile stress. The variable stiffness unit 60d includes: a coil pipe 62d; a core wire 63d passing slidably through a hollow inner part of the coil pipe 62d; fixing members 64d and 65d provided at both ends of the core wire 63d, respectively; and washers 66d and 67d provided at both ends of the coil pipe 62d. The variable stiffness unit 60d also includes a nut 71d and a lead screw 72d engaged with the nut 71d. Further, the variable stiffness unit 60d includes a housing 73d covering an end of the lead screw 72d and the fixing member 65d.

In the state shown in the upper part of FIG. 9, the lead screw 72d and the fixing member 65d are apart from each other with a gap. In this state, the core wire 63d is slidable along the longitudinal direction of the coil pipe 62d. In this state, no tensile stress is applied to the core wire 63d when the coil pipe 62d is bent, so that the bending stiffness is low.

In the state shown in the lower part of FIG. 9, the lead screw 72d and the fixing member 65d are in contact with each other. In this state, the core wire 63d cannot move along the longitudinal direction of the coil pipe 62. In this state, a tensile stress is applied to the core wire 63d when the coil pipe 62d is bent, so that the bending stiffness is high.

The stiffness controller 117d includes a drive unit such as a motor (not shown), and can drive the lead screw 72d so as to switch the above-described two states.

Arranging such a variable stiffness unit 60d in the flexible tube section 14 allows varying the bending stiffness of the flexible tube section 14 at a desired position.

As described above, the endoscope 10 may adopt multiple types of variable stiffness units such as the variable stiffness units 60, 60a, 60b, 60c, and 60d capable of varying the bending stiffness by way of the stiffness control executed by the stiffness controllers 117, 117a, 117b, 117c, and 117d.

Referring back to FIG. 1, the input device 30 is a general input device such as a keyboard. The input device 30 is connected to the control device 100 through a cable 23. Various commands for operating the endoscope apparatus 1 are input through the input device 30. The input device 30 may be an operation panel provided to the control device 100 or a touch panel displayed on a display screen.

The display device 40 is a commonly-used monitor such as a liquid crystal display. The display device 40 is connected to the control device 100 through a cable 24. The display device 40 displays an endoscopic image according to a video signal transmitted from the image processor 112 of the control device 100. The display device 40 may also display information regarding the shape of the flexible tube section 14 based on the coordinates of the position of each source coil 52, which are calculated by the shape calculator 115 of the control device 100. The display device that displays an endoscopic image may be either the same as or different from the display device that displays information regarding the shape of the flexible tube section 14.

(Concept of Setting Stiffness Change Range)

A bending stiffness at an apex of a bent shape of the insertion section 11 and at a maximum reaction force position in the insertion section 11, which is an important concept behind changing the bending stiffness of the variable stiffness unit 60 using the stiffness controller 117, will be described.

Figure 10:
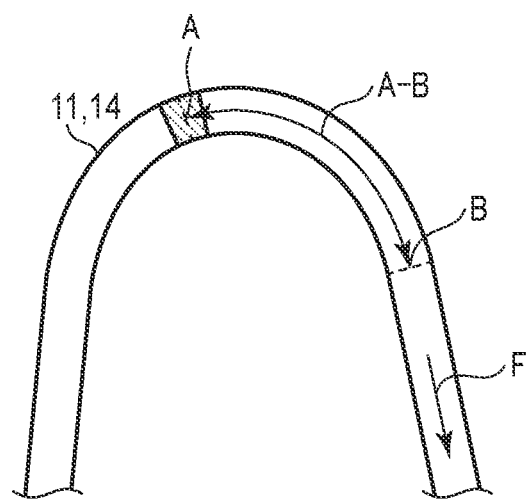
FIG. 10 is a diagram showing a concept of a range in which the bending stiffness of an insertion section is changed.

FIG. 10 shows an example of a predetermined range including the position A of the apex of the bent shape of the insertion section 11, that is, the hatched range around the position A, and a maximum reaction force position B at which a reaction force that the insertion section 11 receives from a subject reaches a maximum in the longitudinal direction of the insertion section 11. Herein, the apex may be a flexure point of the insertion section, a predetermined range including the flexure point, a point at which the bending radius is at a minimum in the bent shape of the insertion section, or a predetermined range including the point at which the bending radius is at a minimum, as will be described later. In the present embodiment, the bending stiffness of the variable stiffness unit 60 (not shown) included in the range A-B indicated by the bidirectional arrow in FIG. 10 is increased by the stiffness controller 117. As a result, a propulsive force F at the distal end of the insertion section is increased to improve the insertability, so that the insertion section 11 can smoothly proceed in the subject.

Hereinafter follows an explanation of the mechanism by which increasing the bending stiffness of the variable stiffness unit 60 within the range A-B leads to improvement of the insertability of the insertion section 11.

The mechanism will be explained by which the insertability of the insertion section 11 is improved by increasing the bending stiffness on the distal side from the position A of the apex of the bent shape of the insertion section 11 or a predetermined range including the apex A. If the insertion section 11 unnecessarily warps when in a bent state, the propulsive force in the proceeding direction is not sufficiently transmitted when the insertion section 11 is pushed in from the manipulating side. In addition, if the bending stiffness of the entire bending section with a bending radius equal to or greater than a predetermined bending radius is increased, the flexible tube section 14 does not bend sufficiently along a bent shape of the subject and may extend the subject. Therefore, the bending stiffness on the distal side with respect to the position A of the apex of the bent shape or a predetermined range including the apex A is increased, so that the insertion section 11 is prevented from unnecessarily warping and the flexible tube section 14 is appropriately bent. Numerical analysis and the like have shown that when the stiffness in the position A of the apex is increased, the propulsive force at the distal end of the insertion section is directed in a desired propelling direction.

Hereinafter follows an explanation of the mechanism by which the insertability of the distal end of the insertion section is enhanced by making the bending stiffness value on the distal side of the insertion section 11 relatively higher than that on the manipulating side of the insertion section 11, based on the relationship between the reaction force that the insertion section 11 receives from the subject 70 and the propulsive force of the insertion section 11.

Figure 11:
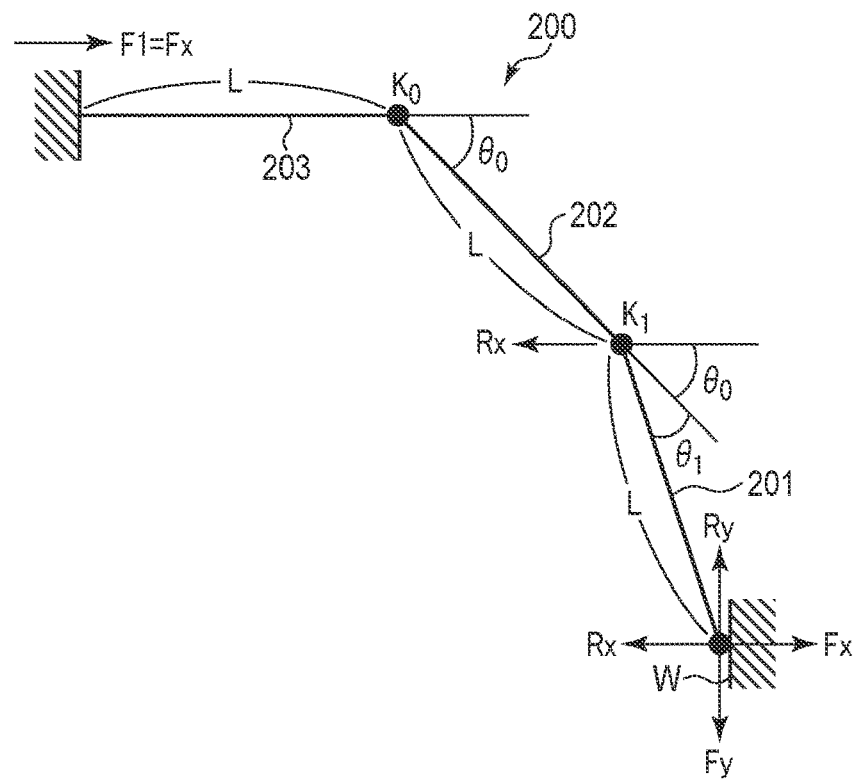
FIG. 11 is a diagram showing the insertion section modeled using a rigid link model.

FIG. 11 shows a rigid link model 200 modeled on the insertion section 11. A rigid link model 200 in which three rigid links 201, 202, and 203 are connected will be discussed. The total length of each rigid link 201, 202, 203 is L. It is assumed that the rigid link model 200 is in a state where a force F1 has been applied to the proximal end of the rigid link 203 on the manipulating side, and the distal end of the rigid link 201 on the distal side has collided with a wall W simulating the bowel wall being the subject. A case where a propulsive force Fy of the distal end of the rigid link 201 is increased in this state will be considered. The torque balance in FIG. 11 is expressed by following equations (1) and (2):

$$T_0 = K_0 \theta_0 = Rx \cdot L \sin \theta_0 \cdot Ry \cdot L \cos \theta_0 + T_1, \quad (1)$$

$$T_1 = K_1 \theta_1 = Rx \cdot L \sin(\theta_0 + \theta_1) - Ry \cdot L \cos(\theta_0 + \theta_1), \quad (2)$$

where $T_0$ and $T_1$ denote torques of rotating sections between the rigid links 203 and 202 and between the rigid links 202 and 201, respectively; $K_0$ and $K_1$ denote rotational spring stiffness values, for example, rotational spring constants; $\theta_0$ and $\theta_1$ denote the rotational angles shown in FIG. 11, respectively; Fx denotes a force applied to the wall W by the rigid link 201; Rx denotes a reaction force of Fx(=F1); and Ry denotes a reaction force of the propulsive force Fy. When the reaction forces Rx and Ry are solved from the equations (1) and (2), following equations (3) and (4) are obtained:

$$Rx = \{T_1 \cos \theta_0 + (T_1 - T_0)\cos(\theta_0 + \theta_1)\}/L \sin \theta_1, \quad (3)$$

$$Ry = \{T_1 \sin \theta_0 + (T_1 - T_0)\sin(\theta_0 + \theta_1)\}/L \sin \theta_1. \quad (4)$$

Based on the action-reaction law, Fx=Rx=F1 and Fy=Ry. Substituting $T_0 = K_0 \theta_0$ and $T_1 = K_1 \theta_1$ into equations (3) and (4) yields equation (5):

$$Fy = Ry = \{K_1 \theta_1 (\sin \theta_0 + \sin(\theta_0 + \theta_1)) - K_0 \theta_0 \cdot \sin(\theta_0 + \theta_1)\}/L \sin \theta_1. \quad (5)$$

It is understood from equation (5) that in order to increase the propulsive force Fy of the distal end of the rigid link 201, the rotational spring stiffness value may be $K_1 > K_0$. In the rigid link model 200, if the bending stiffness value of the rigid link on the distal side is larger than the bending stiffness value of the rigid link on the proximal side, the propulsive force Fy increases. In this case, the reaction force Rx from the intestinal wall also increases. That is, if the reaction force from the intestinal wall is high, the propulsive force is also high.

Figure 12:
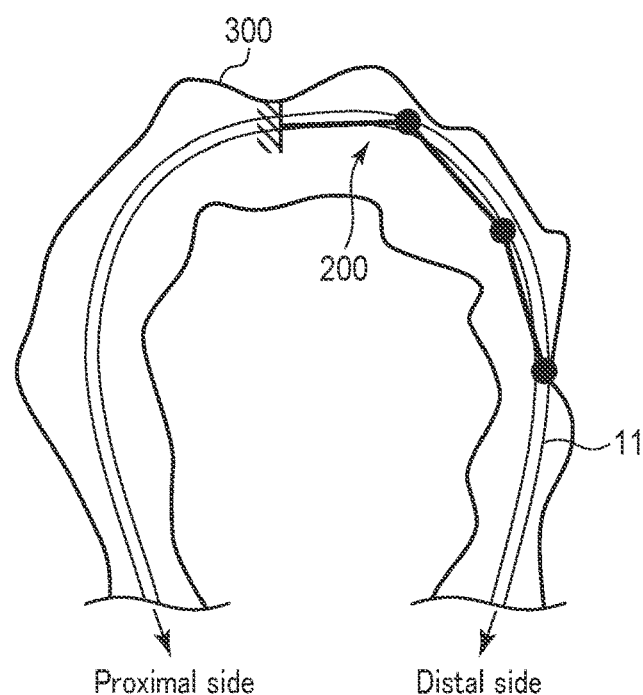
FIG. 12 is a diagram showing a concept of modeling the insertion section at the time of insertion into a subject using a rigid link model.

FIG. 12 is a diagram showing a concept of modeling the insertion section 11 inserted into the subject using the above-described rigid link model 200. Based on the above-described theory, if the rotational spring stiffness value $K_1$ is set to be larger than the rotational spring stiffness value $K_0$, that is, if the bending stiffness of the distal side of the insertion section 11 is set to be higher than the bending stiffness of the proximal side of the insertion section 11, the propulsive force of the distal end of the insertion section 11 increases. Therefore, the insertion section 11 is easily advanced, improving the insertability of the insertion section 11.

As described above, in the present embodiment, the bending stiffness value of the flexible tube section 14 is set to be relatively higher on the distal side from the apex A of the bent shape of the flexible tube section 14, or a predetermined range including the apex A, than on the proximal side, that is, the manipulating side. As a result, the propulsive force of the distal end of the insertion section is increased to improve the insertability.

However, increasing the bending stiffness value of the entire part of the flexible tube section 14 from the apex A to the distal end of the flexible tube section 14 is not necessarily effective in improving the insertability. It is desirable to appropriately set a range in which the insertability is improved by increasing the bending stiffness.

Hereinafter, a case will be considered where with the apex A of the bent shape of the insertion section 11 or a predetermined range including the apex A set as a start point, and a predetermined position on the distal side from the apex A or the predetermined range including the apex A set as an end point, the bending stiffness in the range from the start point to the end point is increased. With the apex A of the bent shape or a predetermined range including the apex A set as a start point of the stiffness change range, discussion will take place as to an optimal position on the distal side from the start point that can be set as an end point of the stiffness change range based on numerical analysis results.

Figure 13:
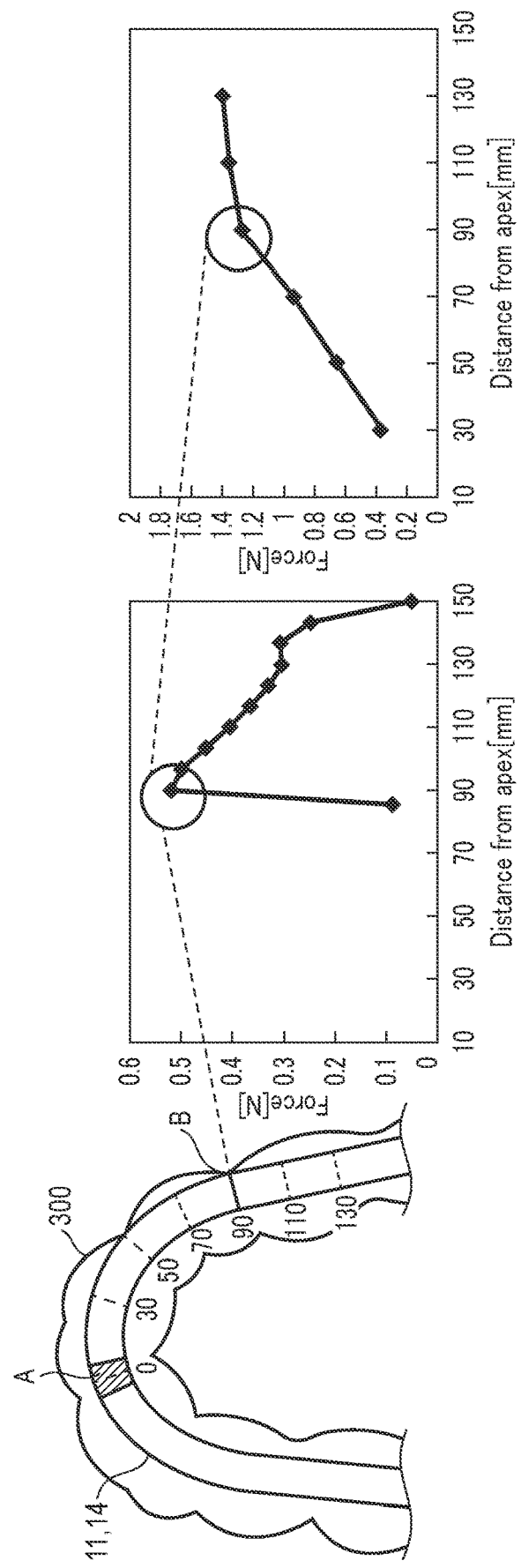
FIG. 13 is a diagram showing an example of a relationship between a distance from an apex of a bent shape of the insertion section and a reaction force, and a relationship between the distance from the apex of the bent shape of the insertion section and a propulsive force.

The left side of FIG. 13 shows a state in which the insertion section 11 having a uniform bending stiffness value is inserted into an intestinal wall 300 as a subject and is bent. Herein, the distance from the apex A along the longitudinal direction of the insertion section 11 is defined with the apex A of the curve of the insertion section 11 set as 0.

The center of FIG. 13 shows an example of the numerical analysis result of the relationship between the position in the longitudinal direction of the insertion section 11 and the reaction force that the insertion section 11 receives from the intestinal wall 300, in the bent insertion section 11 shown on the left side of FIG. 13. The reaction force applied to the insertion section 11 reaches a maximum at a distance of 90 [mm] from the apex, for example.

The right side of FIG. 13 shows an example of the numerical analysis result of the relationship between the position in the longitudinal direction of the insertion section 11 and the propulsive force of the insertion section 11 when the bending stiffness from the apex A to a predetermined distance is increased in the states shown on the left side and the center of FIG. 13. That is, an example is shown of the propulsive force when the bending stiffness in the range from the apex A to a distance of 30, 50, 70, 90, 110, and 130 [mm] is increased when the maximum reaction force position B is at a distance of 90 [mm] from the apex. In other words, an example is shown of the propulsive force when the position of the end point of the stiffness change is varied. The propulsive force varies according to the position of the end point of the stiffness change.

The inventors of the present invention have found that the position at which the reaction force reaches a maximum is correlated with the position at which the propulsive force starts to be constant, as can be seen from the graphs shown in the center and on the right side of FIG. 13. In particular, as can be seen from the graph on the right side of FIG. 13, when a comparison is made between the proximal side from the maximum reaction force position B (for example, a position where the distance from the apex A is less than 90 [mm]), and the distal side from the maximum reaction force position B (for example, a position where the distance from the apex A is 90 [mm] or more), it is found that whereas the magnitude of the propulsive force is proportional to the distance from the apex A on the proximal side, the magnitude of the propulsive force hardly changes and is close to a constant value, that is, the propulsive force is likely to converge, on the distal side. It is considered that the propulsive force as a whole hardly changes for the following reason: although the propulsive force of the insertion section 11 increases in the range from the apex A to the maximum reaction force position B, for example, the bending of the insertion section 11 is small on the distal side from that range, that is, the propulsive force added on the distal side from the maximum reaction force position B is small.

Figure 14:
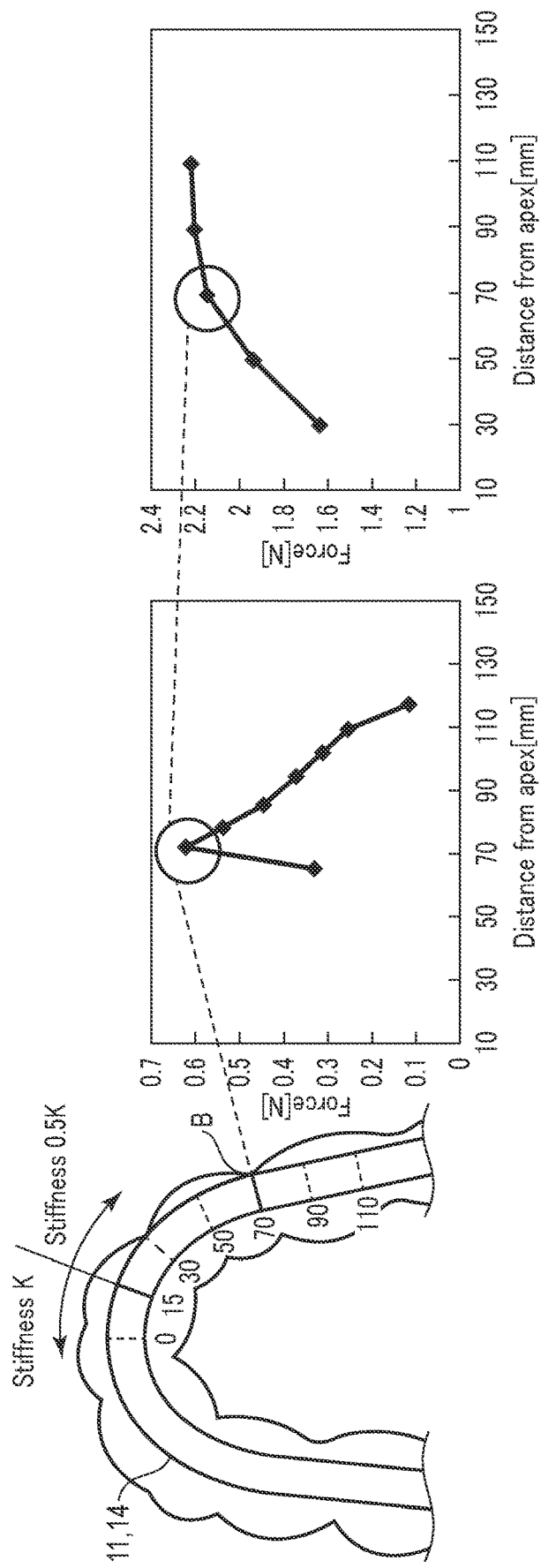
FIG. 14 is a diagram showing an example of a relationship between a distance from an apex of a bent shape of the insertion section and a reaction force, and a relationship between the distance from the apex of the bent shape of the insertion section and a propulsive force.

The left side of FIG. 14 shows a state in which the insertion section 11 having different bending stiffness values on the distal side and the proximal side is inserted into the intestinal wall 300 as a subject and is bent. Herein, it is assumed that the bending stiffness value of the flexible tube section 14 on the proximal side from the position at a distance of 15 [mm] from the apex is K, and that the bending stiffness value of the flexible tube section 14 on the distal side from that position is 0.5 K. Also, the distance from the apex A along the longitudinal direction of the insertion section 11 is defined with the apex A of the curve of the insertion section 11 set to 0.

The center of FIG. 14 shows an example of the numerical analysis result of the relationship between the position in the longitudinal direction of the insertion section 11 and the reaction force that the insertion section 11 receives from the intestinal wall 300, in the bent insertion section 11, shown on the left side of FIG. 14. The reaction force applied to the insertion section 11 reaches a maximum at a distance of 70 [mm] from the apex, for example.

The right side of FIG. 14 shows an example of the numerical analysis result of the relationship between the position in the longitudinal direction of the insertion section 11 and the propulsive force of the insertion section 11 when the bending stiffness from the apex A to a predetermined distance is increased in the states shown on the left side and the center of FIG. 14. That is, an example is shown of the propulsive force when the bending stiffness in the range from the apex A to a distance of 30, 50, 70, 90, and 110 [mm] is increased when the maximum reaction force position B is at a distance of 70 [mm] from the apex.

In FIG. 14, both the position at which the reaction force reaches a maximum and the position at which the propulsive force starts to be constant are at a distance of 70 [mm] from the apex. That is, it has been found that the maximum reaction force position and the position at which the propulsive force starts to be constant are correlated with each other, as also explained with reference to FIG. 13.

As described above, regardless of the distribution of the bending stiffness of the insertion section 11, there is a correlation between the position at which the reaction force received from the intestinal wall reaches a maximum and the position at which the propulsive force starts to be constant. A high propulsive force can also be obtained when the stiffness of the insertion section 11 from the apex to a position at the distal end with respect to the maximum reaction force position is increased. However, even when the position of the end point of the stiffness change is set on the distal side from the maximum reaction force position, the effect of increasing the propulsive force does not increase with the extension of the position of the end point. If the bending stiffness in the range from the apex to the maximum reaction force position is increased, it is possible to obtain a sufficiently high propulsive force in the same manner as in the case where the bending stiffness in the range from the apex to the distal side from the maximum reaction force position is increased.

Therefore, the range A-B between the position A of the apex of the bent shape of the insertion section 11 and the maximum reaction force position B is at least effective for increasing the bending stiffness to improve the insertability, that is, the range A-B is an effective range. For example, if the range for increasing the stiffness is too long, the range of increased stiffness may reach the next flexure of the subject, for example, the descending sigmoid colon junction (the so-called SD-junction) after the top of the sigmoid colon (the so-called S-top) in the case of the large intestine. In this case, the hard insertion section 11 approaches the flexure, likely causing degradation of the insertability. It is more effective if the stiffness controller 117 controls the stiffness of the variable stiffness unit 60, so as to increase the bending stiffness of the variable stiffness unit 60 positioned between the apex A of the bent shape of the insertion section 11 and the maximum reaction force position B.

The setting of a more preferred effective range will be further discussed below with reference to FIG. 15.

Figure 15:
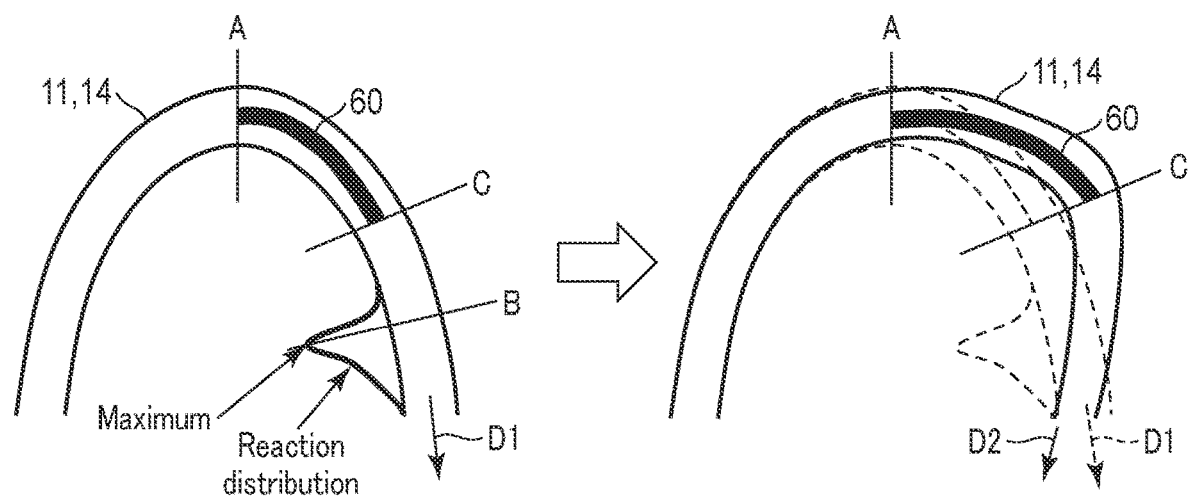
FIG. 15 is a diagram showing a concept of a range in which the bending stiffness of the insertion section is changed.

The state shown on the left side of FIG. 15 is a bent state of the insertion section 11 before the bending stiffness of the insertion section 11 is changed. The position A of the apex of the bent shape of the insertion section 11, and a distribution of the reaction force that the insertion section 11 receives from the subject as well as the maximum reaction force position B are shown. For example, it is assumed that the bending stiffness of the variable stiffness unit 60 extending in the range A-C in the longitudinal direction of the insertion section 11 in the effective range A-B is increased. Herein, the position C is on the manipulating side, that is, the proximal side from the maximum reaction force position B. Also, the arrow indicated by D1 indicates a desirable proceeding direction of the insertion section 11.

When the bending stiffness of the variable stiffness unit 60 extending between A and C is increased from the above-described state, the insertion section 11 may be in the state shown on the right side of FIG. 15, for example. That is, when the bending stiffness of the variable stiffness unit 60 extending between A and C is increased, the insertion section 11 may have a bent shape around the position C. In such a shape, the direction D2 of the distal end of the insertion section may be different from the desired proceeding direction D1 of the insertion section 11. In order to propel the insertion section 11 in a desired propelling direction, it is more effective to increase the bending stiffness from the position of the apex of the insertion section 11 to the position where the reaction force reaches a maximum on the distal side from the apex of the insertion section 11. For example, it is effective to increase the bending stiffness of the entire section between A and B by providing variable stiffness units 60 in the entire flexible tube section 14.

It should be noted that the propulsive force is increased by increasing the bending stiffness of a variable stiffness unit 60 positioned between A and B without increasing the bending stiffness of the entire section between A and B.

Figure 16:
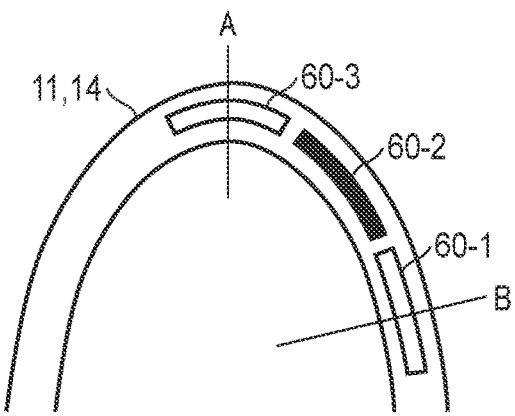
FIG. 16 is a diagram showing an example of a change in the stiffness of the variable stiffness unit.
Figure 17:
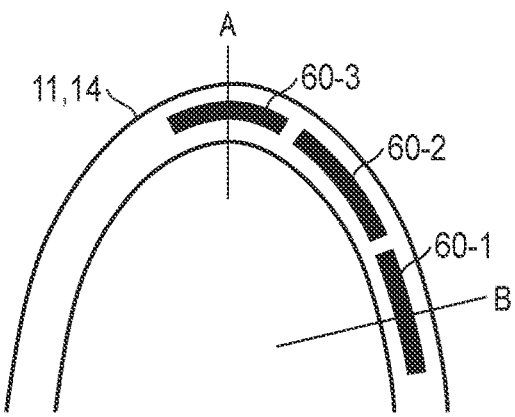
FIG. 17 is a diagram showing an example of a change in the stiffness of the variable stiffness unit.

The range A-B suitable for increasing the propulsive force of the insertion section 11 and the variable stiffness unit 60 in this range will be further described. FIGS. 16 and 17 show, as an example, three variable stiffness units 60-1, 60-2, and 60-3 provided in the flexible tube section 14 of the insertion section 11. Among these three variable stiffness units, the variable stiffness unit 60-1 on the most distal side extends over the maximum reaction force position B, and the variable stiffness unit 60-3 on the most proximal side extends over the apex A. In other words, the variable stiffness units 60-1 and 60-3 are positioned across the boundary of the range A-B suitable for increasing the propulsive force of the insertion section 11. The variable stiffness unit 60-2 is positioned within the range A-B.

In such a case, at least the stiffness of the variable stiffness unit 60-2 is increased. The stiffness of the variable stiffness units 60-1 and 60-3 may not be increased. In FIG. 16, the stiffness of the variable stiffness unit 60-2 shown in black is increased, and the stiffness of the variable stiffness units 60-1 and 60-3 not shown in black is not increased. The propulsive force can be increased by increasing the stiffness of the variable stiffness unit 60-2 positioned within the range A-B. Also, not increasing the stiffness of the variable stiffness units 60-1 and 60-3 does not decrease the propulsive force.

The stiffness of the variable stiffness units 60-1 and 60-3 may be increased. In FIG. 17, the stiffness of the three variable stiffness units 60-1, 60-2, and 60-3 shown in black is increased. In addition to the stiffness of the variable stiffness unit 60-2, the stiffness of the variable stiffness units 60-1 and 60-3, at least a part of which is included in the range A-B, is increased, so that the propulsive force can be further increased.

Figure 18:
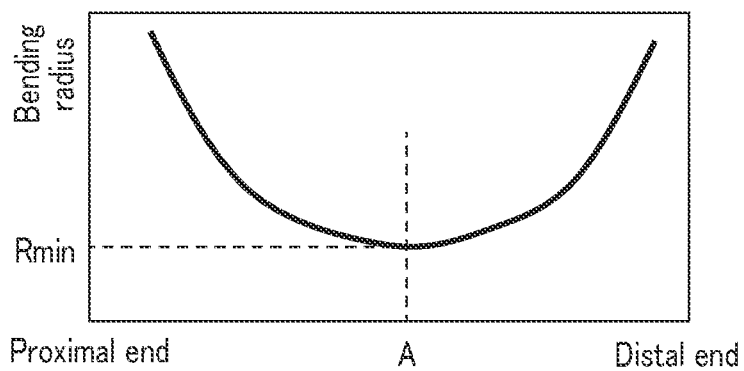
FIG. 18 is a diagram for explaining an example of a flexure point for setting a range in which the bending stiffness of the insertion section is changed.
Figure 19:
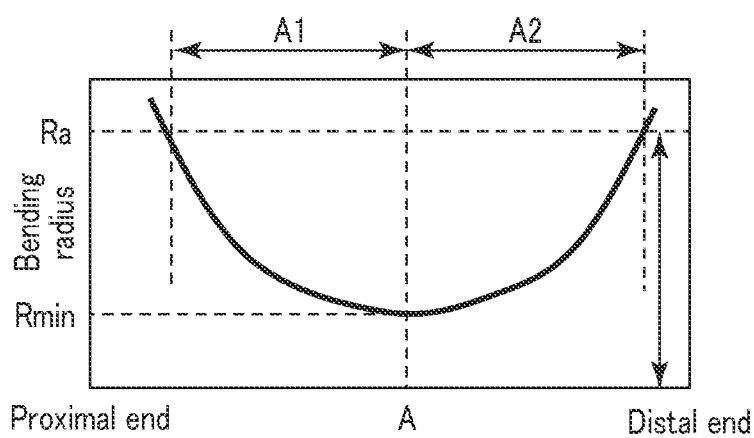
FIG. 19 is a diagram for explaining an example of a flexure point for setting a range in which the bending stiffness of the insertion section is changed.

FIG. 18 is a diagram showing an example of the relationship between the position in the longitudinal direction of the insertion section 11 and the bending radius of the insertion section 11. The above-described apex A may be a position of the radius Rmin at which the bending radius reaches a minimum in the bent shape of the insertion section 11. Alternatively, a range including the regions A1 and A2 in which the bending radius is equal to or smaller than a predetermined value Ra may be regarded as the apex, as shown in FIG. 19.

Figure 20:
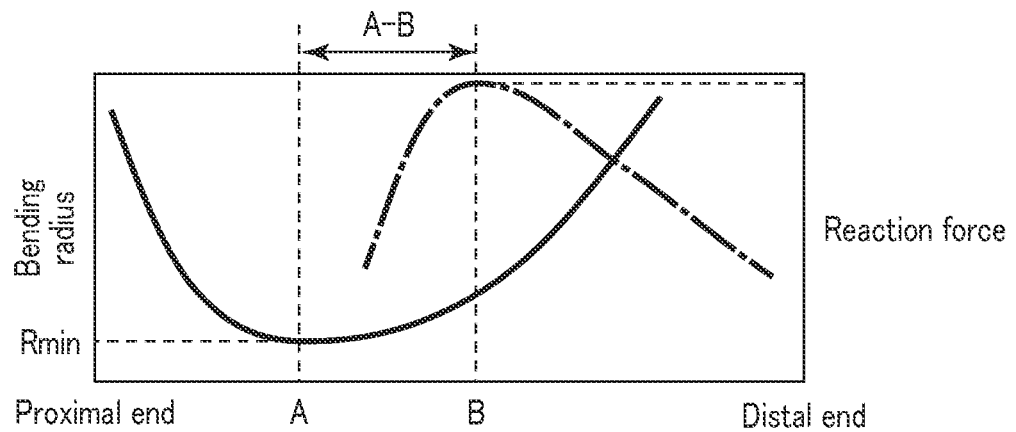
FIG. 20 is a diagram for explaining an example of a flexure point, which corresponds to a range in which the bending stiffness of the insertion section is changed, and a maximum reaction force position.

FIG. 20 is a diagram showing an example of the relationship among the position in the longitudinal direction of the insertion section 11, the bending radius of the insertion section 11, and the reaction force that the insertion section 11 receives from the subject. The bending radius is indicated by a solid line, and the reaction force is indicated by a dashed-and-dotted line. Herein, the range A-B from the position A, where the bending radius has a minimum value Rmin, to the position B, where the reaction force is at a maximum, is an effective range for increasing the bending stiffness to improve the insertability. The apex A may be a point having a characteristic with respect to the bent shape, such as a flexure point, a point at which the bending radius is at a minimum or a periphery thereof, or a central position of the bent shape or a periphery thereof. By increasing the bending stiffness of the variable stiffness unit 60 positioned within this range, the propulsive force of the insertion section is increased and the insertability is improved.

(Operation of Endoscope Apparatus)

The operation of the endoscope apparatus 1 will be described. In the description provided below, the endoscope 10 is a large intestine endoscope and the subject is a large intestine, for example. At the start of insertion, the flexible tube section 14 has a predetermined initial bending stiffness value, and the hardness thereof is not a maximum bending stiffness value of the variable stiffness unit 60. That is, each segment of the flexible tube section 14 can be made harder after insertion than at the start of insertion.

The insertion section 11 of the endoscope 10 is inserted into the large intestine, that is, inserted from the anus into the rectum and the colon by the operator. The insertion section 11 proceeds inside the intestinal tract while curving in accordance with the bent shape of the intestinal tract. The endoscope 10 converts light from an object in the intestinal tract into an electric signal by the imaging element 25 of the distal end hard section 12. Then, the electric signal is transmitted to the control device 100. The image processor 112 of the control device 100 acquires the electric signal and converts the acquired electric signal into a video signal. Then, the display controller 113 of the control device 100 displays an endoscopic image based on the video signal on the display device 40.

During the insertion, the coil controller 114 of the control device 100 causes a voltage to be applied from its coil output section to each source coil 52. Thereby, each source coil 52 generates a weak magnetic field around the source coil 52. That is, information on the position of the source coil 52 is output from each source coil 52. The antenna 54 detects the magnetic field generated by the source coil 52 and outputs a detection signal to the shape calculator 115.

Figure 21:
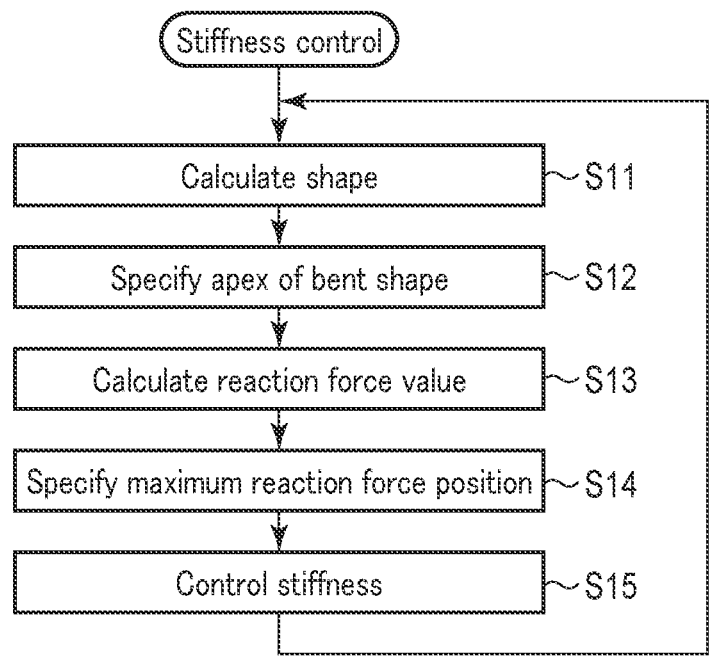
FIG. 21 is a diagram showing an example of a flow of stiffness control.

Hereinafter, an example of a flow of the stiffness control executed by the control device 100 following the aforementioned output to the shape calculator 115 will be described with reference to FIG. 21.

In step S11, the shape calculator 115 receives the detection signal from the antenna 54 at the receiver, and calculates the shape of the insertion section 11 based on the detection signal.

The display controller 113 may generate an image corresponding to the calculated shape based on the calculated shape and cause the display device 40 to display the image.

In step S12, the shape calculator 115 specifies the position of the apex of the bent shape in the calculated shape. The position of the apex may be specified by calculating a value of a curvature or a radius of curvature at each position in the longitudinal direction of the bent shape, for example, a value of a bending radius shown in FIG. 18.

In step S13, the reaction force calculator 116 acquires the shape information calculated by the shape calculator 115 and the current stiffness value of the variable stiffness unit 60, and calculates the value of the reaction force that the insertion section 11 receives from the subject 70 based on the acquired shape and current stiffness value. Various methods may be adopted to calculate the reaction force, and the reaction force may be obtained, for example, dynamically or through numerical analysis based on the concept described with reference to FIG. 11.

Hereinafter, an example of a method for calculating the reaction force will be described.

For example, the reaction force calculator 116 calculates the value of the reaction force that the flexible tube section 14 receives from the subject 70 for each segment of the flexible tube section 14 based on the detection principle that "a first bending moment Mb estimated from the shape information and the bending stiffness" is nearly equal to "a second bending moment Mf estimated from a force applied from the outside".

This is based on equilibrium of static force and the premise that the movement of the insertion section 11 and the subject 70 is gentle. Other than the equilibrium of the bending moment, the reaction force may be calculated based on the detection principle that "a first internal force estimated from the deformation state of the insertion section 11" is nearly equal to "a second internal force estimated from a force applied from the outside". The internal force may be, for example, an axial force, a shear force, a torsional moment, or the like.

Hereinafter, calculation of the reaction force based on the detection principle that "a first bending moment Mb estimated from the shape information and the bending stiffness" is nearly equal to "a second bending moment Mf estimated from a force applied from the outside" will be described.

Figure 22:
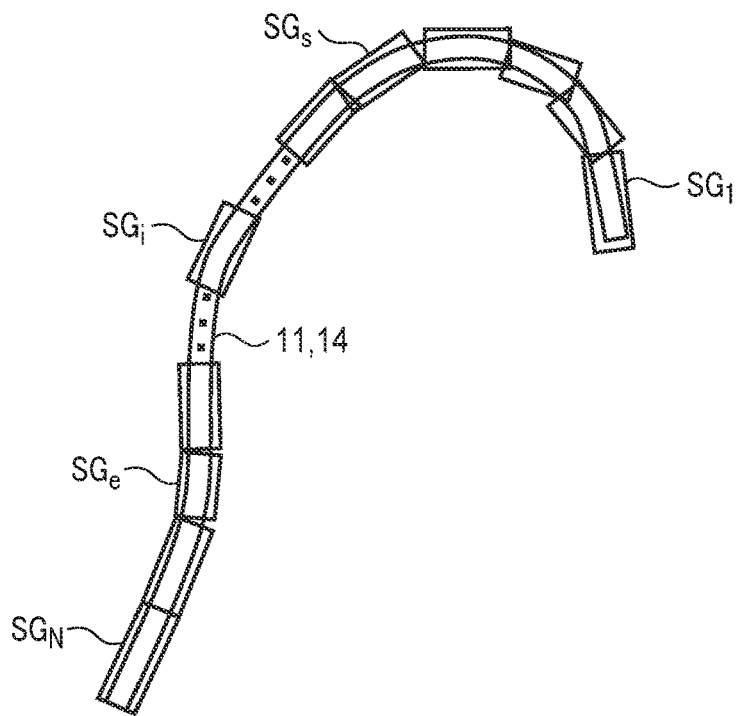
FIG. 22 is a diagram showing an example of a manner in which the insertion section is segmented.

FIG. 22 shows the segmented insertion section 11. It is assumed that the insertion section 11 is segmented into N segments from segment $SG_1$ on the distal side to segment $SG_N$ on the manipulating side. Of these segments, $N_s$ segments from segment $SG_s$ to segment $SG_e$ are calculation targets.

A calculation of the first bending moment Mb in the case of two dimensions will be described for simplification. It is assumed that each segment is straight when no bending moment is applied.

Figure 23:
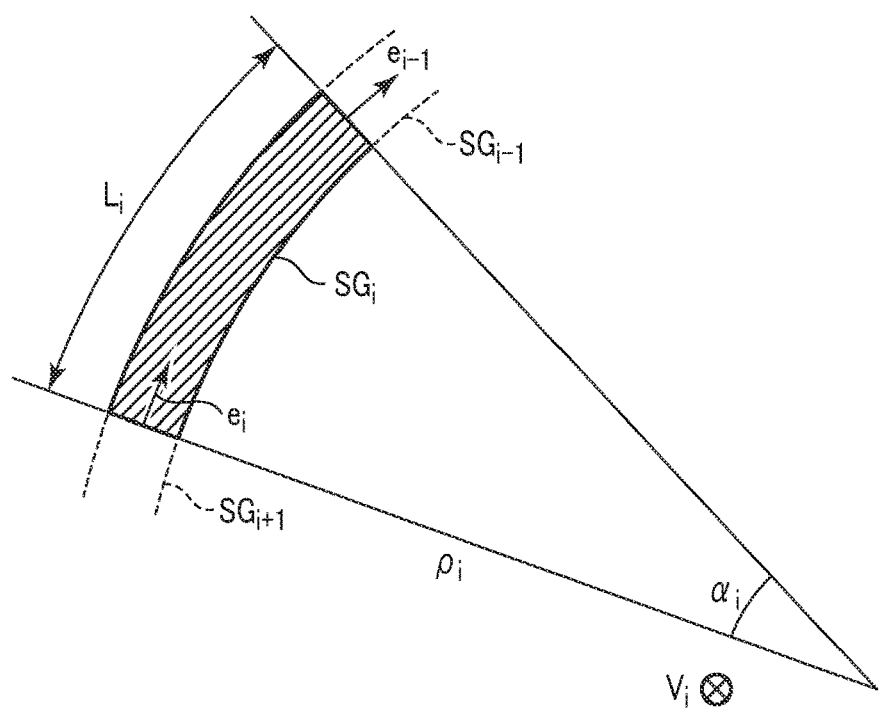
FIG. 23 is a diagram showing an example of a bent shape of a segment $SG_i$.

FIG. 23 shows a bent shape of the segment $SG_i$, which is the i-th segment. The shape of the segment $SG_i$ is approximated to a circular arc.

Herein, the definition is made as described below. In the definition provided below, the letter "i" is a suffix corresponding to the segment $SG_i$;

Bending moment estimated from shape: $Mb_i$,
Young's modulus: $E_i$,
Second moment of area: $I_i$,
Directional vector of segment $SG_i$: $e_i$,
where the directional vector $e_i$ denotes a directional vector at a connection section between segment $SG_{i+1}$ and the segment $SG_i$, and is directed to the segment $SG_{i-1}$ side;
Directional vector perpendicular to the sheet of drawing: $V_i$,
Curvature: $\chi_i(=1/\rho_i)$,
where $\rho_i$ denotes a radius of curvature;
Bending stiffness: $G_i(=E_i \cdot I_i)$,
For a discretionarily selected segment $SG_i$, the following relationship is established based on the material mechanics:

$$Mb_i = E_i / \rho_i \cdot I_i, \quad (6)$$

$$\alpha_i = L_i / \rho_i, \quad (7)$$

where $\alpha_i$ denotes an angle [rad].
From equations (6) and (7), the following relationship is derived:

$$Mb_i = (\alpha_i / L_i) \cdot (E_i \cdot I_i) = \chi_i \cdot G_i. \quad (8)$$

Herein, "$E_i \cdot L_i = G_i$" is called bending stiffness.

The bending moment $Mb_i$ in the segment $SG_i$, which is estimated from the shape information, is obtained from equation (8).

It is assumed that, in two dimensions, when the segment $SG_{i-1}$ side near the distal end of the insertion section 11 is bent counterclockwise, the bending moment $Mb_i$ is $Mb_i > 0$ and the angle $\alpha_i$ is $\alpha_i > 0$.

In the case of three dimensions, the bending direction may be a direction in which the bending is performed around a direction perpendicular to the drawing sheet or a direction perpendicular to both the directional vectors $e_i$ and $V_i$. Here, the bending moment $Mb_i$ is expressed as a combination of a scalar and the above-described direction or as a vector.

A specific calculation of the second bending moment Mf will be described with reference to a case where a single force acts on the insertion section 11 for simplification. In FIG. 24, the second bending moment $Mf_i$ applied to the segment $SG_i$ by an external force is, dynamically speaking, as described below.

<<Case of Two Dimensions (XY Coordinates)>>

When the position to which a pressing force F, which is a vector here, is applied is on the distal side from the position of the segment $SG_i$, the second bending moment $Mf_i$ is as shown below. Note that the second bending moment $Mf_i$ is a scalar, and is set to a value+when the bending moment is a counterclockwise bending moment.

$$Mf_i = z\text{-component of } (d_i \times F), \quad (9a)$$

where "×" denotes outer product, and $d_i$ denotes a vector from the center of the segment $SG_i$ to the position to which the pressing force F is applied.

Alternatively, the following equation may be adopted:

$$Mf_i = |d_i \times F| \text{ (absolute value).}$$

When the position to which the pressing force F is applied is on the manipulating side from the position of the segment $SG_i$, the second bending moment $Mf_i$ is as follows:

$$Mf_i = 0. \tag{9b}$$

This is a scalar.

<<Case of Three Dimensions>>

When the position to which the pressing force F, which is a vector here, is applied is positioned on the distal side from the position of the segment $SG_i$, the second bending moment $Mf_i$ is as described below: Note that the second bending moment $Mf_i$ is a vector;

$$Mf_i = d_i \times F. \tag{9c}$$

When the position to which the pressing force F is applied is on the manipulating side from the position of the segment $SG_i$, the second bending moment $Mf_i$ is as follows:

$$Mf_i = 0. \tag{9d}$$

This is zero vector. Zero vector refers to a vector with a magnitude of 0.

Next, a case where multiple forces act on the insertion section 11 will be described. When multiple forces act, the resultant force of the multiple forces may be calculated for a pressing force $F_j$, which is applied to a position on the distal side from the position of the segment $SG_i$. When the force is a distributed load, it may be considered that the force is concentrated on specific multiple points, as described later.

<<Case of Two Dimensions (XY Coordinates)>>

In this case, the second bending moment $Mf_i$ is as follows:

$$Mf_i = \text{z-component of } [\Sigma(d_{ij} \times F_j)]. \tag{10a}$$

Note that only the force on the distal side from the position of the segment $SG_i$ is calculated.

Where, $F_j$ denotes an external force (vector), and "×" denotes an outer product.

Alternatively, the following equation may be adopted:

$$Mf_i = |\Sigma(d_{ij} \times F_j)| \text{ (absolute value).}$$

<<Case of Three Dimensions>>

In this case, the second bending moment $Mf_i$ is as follows:

$$Mf_i = \Sigma(d_{ij} \times F_j). \tag{10b}$$

Note that only the force on the distal side from the position of the segment $SG_i$ is calculated.

For example, the reaction force calculator 116 calculates at least one of the position, the direction, and the magnitude of the reaction force based on the relationship $Mf_i \approx Mb_i$ between the first bending moment $Mb_i$ and the second bending moment $Mf_i$ described above. For example, at least one of the position to which the pressing force F or $F_j$ is applied, the direction of the pressing force F or $F_j$, and the magnitude of the pressing force F or $F_j$ is calculated.

The reaction force calculator 116 may calculate the value of the reaction force that the insertion section 11 receives from the subject 70 in step S13 by adopting the method described as an example above.

In step S14, the reaction force calculator 116 acquires a distribution of the reaction force values along the longitudinal direction of the flexible tube section 14, on the distal side from the apex in the bent shape calculated by the shape calculator 115, and specifies the maximum reaction force position at which the reaction force value is at a maximum.

In step S15, the stiffness controller 117 controls the stiffness of the variable stiffness unit 60 so as to increase the bending stiffness of the variable stiffness unit 60 positioned between the apex specified by the shape calculator 115 and the maximum reaction force position specified by the reaction force calculator 116. At this time, the stiffness controller 117 controls the stiffness of the variable stiffness unit 60 so as to maintain a state in which the region between the apex and the maximum reaction force position is bent. After step S15, the process returns to step S11, and step S11 and the subsequent steps are repeated.

As described above, in the endoscope apparatus 1, the stiffness controller 117 drives the variable stiffness unit 60 to change the bending stiffness of the flexible tube section 14, based on the information on the bent shape and the information on the reaction force of the flexible tube section 14 during the insertion.

Figure 25:
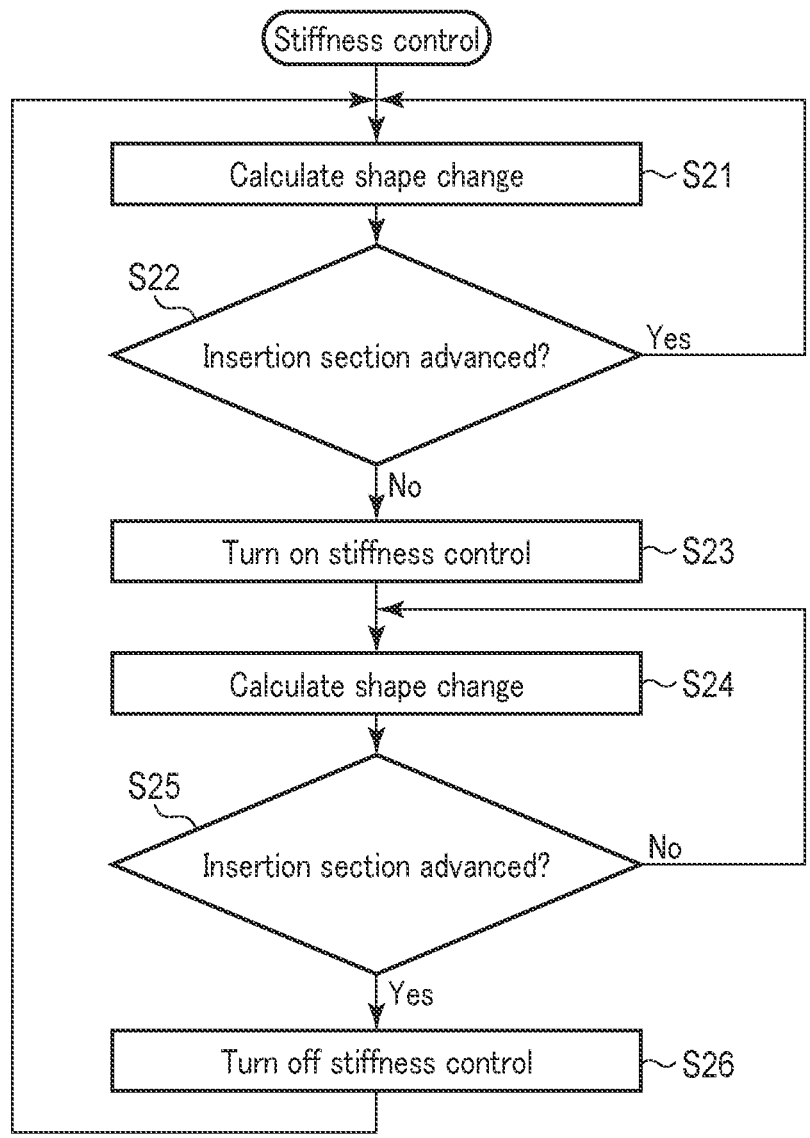
FIG. 25 is a diagram showing an example of a flow of stiffness control.

FIG. 25 is a diagram illustrating another example of the flow of the stiffness control executed by the control device 100.

In step S21, the shape calculator 115 detects a change in the shape of the insertion section 11, for example, a change in the shape of the flexible tube section 14, based on the state information acquired from each source coil 52 and the antenna 54 as the shape detector. The change in the shape can be detected, for example, by comparing the shape of the insertion section 11 at a certain time with the shape of the insertion section 11 at a time after the certain time.

In step S22, the control device 100 determines whether or not the insertion section 11 has advanced using a determination unit (not shown). Information on the change in the shape of the flexible tube section 14 calculated in step S21 may be used to determine whether or not the insertion section 11 has advanced.

If it is determined that the insertion section 11 has advanced (Yes in step S22), the process returns to step S21. If it is determined that the insertion section 11 has not advanced (No in step S22), the process proceeds to step S23.

In step S23, the stiffness controller 117 turns on the stiffness control. Thereby, the process shown in FIG. 21 is performed, for example, so that the stiffness of the variable stiffness unit 60 is controlled so as to increase the stiffness of the variable stiffness unit 60 positioned between the apex A of the bent shape and the maximum reaction force position B.

In step S24, the shape calculator 115 detects the change in the shape of the insertion section 11, for example, the change in the shape of the flexible tube section 14, based on the state information acquired from each source coil 52 and the antenna 54 as the shape detector in the same manner as in step S21.

In step S25, the control device 100 determines whether or not the insertion section 11 has advanced using a determination unit (not shown) in the same manner as in step S22. The change in the shape of the flexible tube section 14 calculated in step S24 may be used to determine whether or not the insertion section 11 has advanced.

If it is determined that the insertion section 11 has not advanced (No in step S25), the process returns to step S24. If it is determined that the insertion section 11 has advanced (Yes in step S25), the process proceeds to step S26.

In step S26, the stiffness controller 117 turns off the stiffness control. As a result, the stiffness of the variable stiffness unit 60 whose stiffness has been increased in step S23 is restored. After step S26, the process returns to step S21, and step S21 and the subsequent steps are repeated.

For example, when it is determined that the insertion section 11 has not advanced by being stuck, for example, due to the change in the bent shape of the insertion section 11, the stiffness controller 117 increases the stiffness of the variable stiffness unit 60 positioned between the apex A of the bent shape and the maximum reaction force position B. Then, when it is determined that the insertion section 11 has advanced by being released from the jammed state, or the like, due to a further change in the bent shape, the stiffness of the variable stiffness unit 60 is restored.

The determination of whether or not the insertion section 11 has advanced in steps S22 and S25 may be performed based on detection and analysis of an endoscopic image by the endoscope 10 instead of the detection of the change in the shape in steps S21 and S24.

In FIG. 25, an example in which the stiffness control through switching ON and OFF is performed by the control device 100, that is, automatic stiffness control is shown for the stiffness control; however, the stiffness control through switching ON and OFF may be manually performed by an operator or the like.

Figure 26:
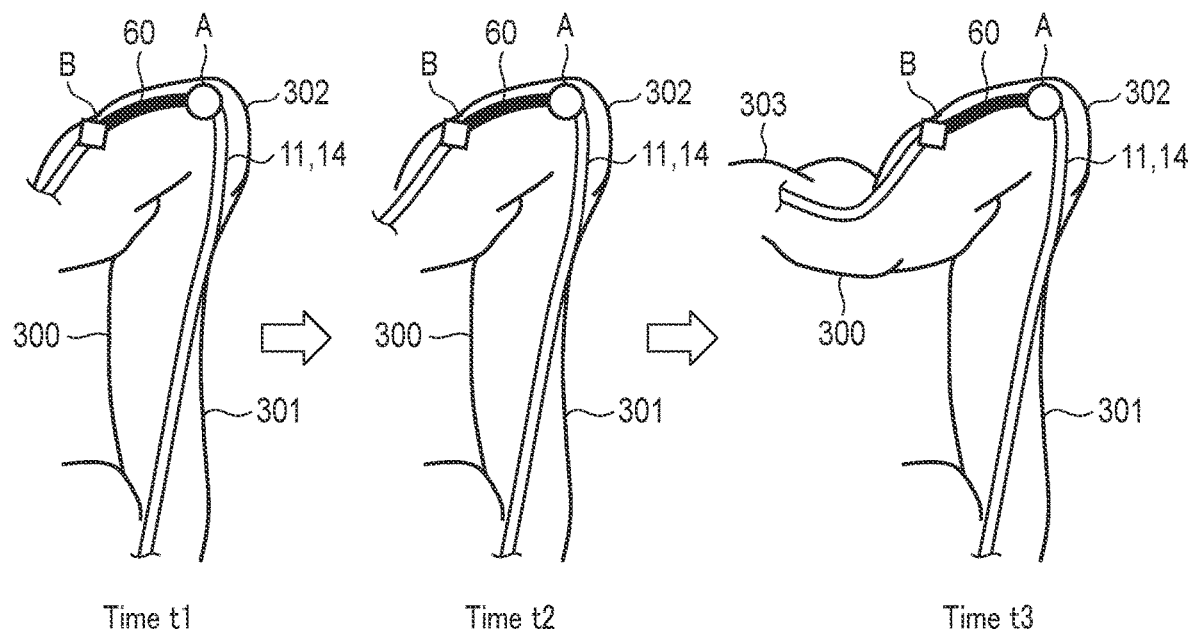
FIG. 26 is a diagram showing an example of stiffness control when the insertion section passes through a splenic flexure.

The stiffness change range may always be at a fixed position with respect to the subject. FIG. 26 shows the insertion section 11 being inserted from the descending colon 301 through the splenic flexure 302 into the left transverse colon 303. For example, at time t1, the stiffness controller 117 controls the stiffness of the variable stiffness unit 60 so that the bending stiffness of the variable stiffness unit 60 positioned between the apex A of the bent shape and the maximum reaction force position B is increased, as shown on the left side of FIG. 26. At time t2 after time t1 as well, the bending stiffness of the variable stiffness unit 60 between A and B is increased, as shown in the center of FIG. 26. Also, at time t3 after time t2, the bending stiffness of the variable stiffness unit 60 between A and B is increased, as shown on the right side of FIG. 26. In this manner, the bending stiffness of the variable stiffness unit 60 positioned between A and B, which is always at a fixed position with respect to the subject, is increased.

Figure 27:
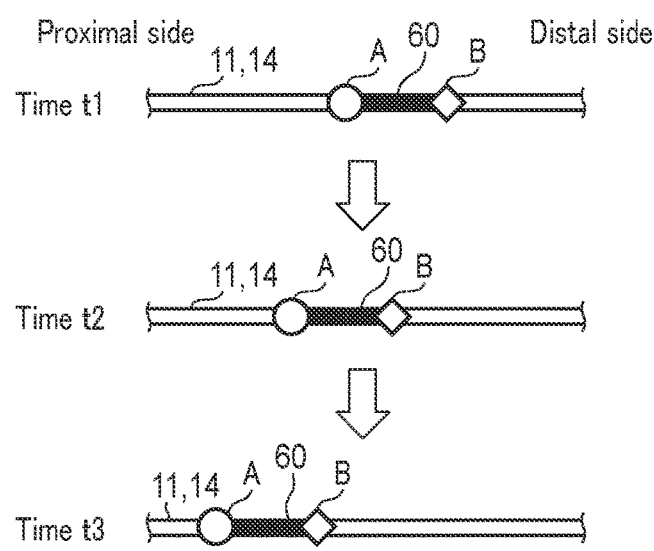
FIG. 27 is a diagram showing a state in which the insertion section shown in FIG. 26 is made linear.

FIG. 27 is a diagram showing the insertion section 11 in a linear shape at each of times t1, t2, and t3 shown in FIG. 26. The apex A of the bent shape and the maximum reaction force position B change with time if the insertion is proceeding smoothly. In FIG. 27, for example, the apex A and the maximum reaction force position B are shifted from the distal side to the proximal side of the insertion section 11 with time. The variable stiffness unit 60 whose bending stiffness is increased by the stiffness controller 117 has only to be within the range A-B.

As described above, according to the present embodiment, the bending stiffness of the variable stiffness unit 60 positioned in a range suitable for increasing the propulsive force of the insertion section 11 is increased based on the reaction force that the insertion section 11 receives from the subject in addition to the bent shape of the insertion section 11. Therefore, the endoscope apparatus 1 having improved insertability can be provided.

Conventionally, a range in which the bending stiffness is increased is set only based on the bent shape of the insertion section 11, for example, detection of a simple curvature or a linear state. However, the curvature of the intestinal tract as a subject, for example, does not necessarily uniformly increase or decrease due to adhesion or the like. Also, the bent shape of the insertion section is not merely a simple bend. Therefore, an appropriate range in which the stiffness is changed may not be determined only by the bent shape.

Also, in some cases, the insertion section 11 may have a so-called "bending tendency" in which the insertion section 11 is bent in a certain direction and does not return to its original state. If the insertion section 11 has the bending tendency, the bending is detected even when the insertion section 11 is not in contact with the intestinal wall. Therefore, an appropriate range in which the stiffness is changed may not be determined only by the bent shape.

In contrast, according to the present embodiment, the stiffness change range is set based on the bent shape of the insertion section 11 and the reaction force from the intestinal wall; thus, it is possible to reliably increase the bending stiffness in a range effective for increasing the propulsive force. In particular, by setting the position on the distal side in the stiffness change range as the maximum reaction force position, the stiffness change range can be set without being too long, and the insertability can be reliably improved.

In addition, when the region between the apex and the maximum reaction force position maintains the bent state as described with reference to FIGS. 11 and 12, it is possible to prevent a decrease in the propulsive force. Therefore, it is more preferable that the stiffness controller 117 control the stiffness of the variable stiffness unit 60 so as to maintain a state in which the region between the apex of the insertion section 11 and the maximum reaction force position is bent.

Second Embodiment

A second embodiment of the present invention will be described with reference to FIG. 28. In the second embodiment, the same components as those in the first embodiment are denoted by the same reference numerals, and description thereof is omitted. Mainly the differences between the second embodiment and the first embodiment will be described below.

Figure 28:
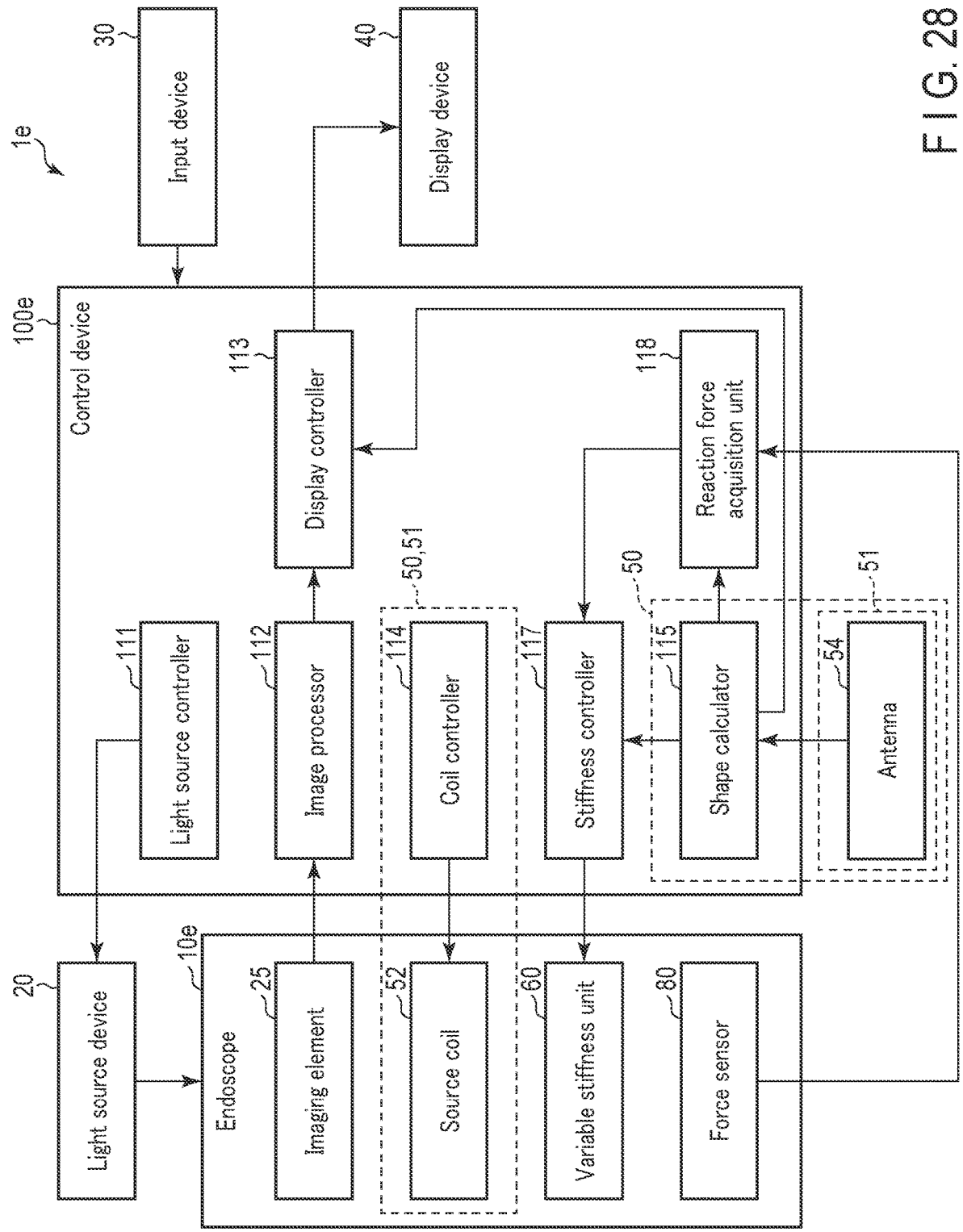
FIG. 28 is a schematic diagram showing an example of an endoscope apparatus according to a second embodiment.

FIG. 28 is a block diagram showing an example of an endoscope apparatus 1e according to the second embodiment. The endoscope apparatus 1e includes an endoscope 10e, a light source device 20, an input device 30, a display device 40, a shape detection device 50, and a control device 100e.

The endoscope 10e includes force sensors 80 in the insertion section 11, for example, in the flexible tube section 14. The force sensor 80 is a sensor configured to directly detect an external force applied from the subject to the insertion section 11. For example, the force sensors 80 are arranged at predetermined intervals along the longitudinal axis direction of the insertion section 11. The force sensor 80 may be a small and thin sensor capable of ultrasensitive detection.

The control device 100e includes a reaction force acquisition unit 118. The reaction force acquisition unit 118 acquires, as a reaction force, the external force detected by the force sensor 80.

In the present embodiment, the control device 100e does not calculate the reaction force. The reaction force acquisition unit 118 functions as a reaction force value specifier configured to acquire, from the detection information of the force sensor 80, a distribution of the reaction force values along the longitudinal direction of the flexible tube section 14 on the distal side from the apex in the bent shape calculated by the shape calculator 115, and specify the maximum reaction force position where the acquired reaction force value is at a maximum.

Even with such a configuration, the propulsive force of the insertion section can be increased by executing the control to increase the bending stiffness of the variable stiffness unit 60 positioned between the apex of the bent shape and the maximum reaction force position, and it is possible to provide a flexible tube insertion apparatus having high insertability.

For example, the elastic modulus of a contacted portion, such as an intestinal tract or an internal organ, into which the insertion section 11 is inserted is not always uniform. That is, even if the amount of displacement of the contacted portion is the same, the reaction force may be different. In such a case, an appropriate range within which the stiffness is changed may not be determined.

On the other hand, in the present embodiment, since the reaction force from the intestinal wall is directly detected by the force sensor 80, it is possible to reliably set a range effective for increasing the propulsive force.

The embodiments of the present invention have been described with reference to the endoscope apparatus 1 including the medical endoscope 10; however, the present invention is not limited to an endoscope apparatus and includes a flexible tube insertion apparatus having a flexible insertion section.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A flexible tube insertion apparatus, comprising:
   a flexible insertion section having a distal end and a proximal end, configured to be inserted into a subject from the distal end, and further configured to bend by receiving a reaction force from the subject when the insertion section comes into contact with the subject;
   an actuator provided at least partially in the insertion section and configured to change a stiffness of the insertion section in a position where the actuator is provided;
   a shape detection sensor configured to detect a bent shape of the insertion section; and
   a processor, wherein the processor is configured to:
      acquire a distribution of values of reaction forces applied to the flexible insertion section distal to an apex of the bent shape of the flexible insertion section and specify a maximum reaction force position at which the value of the reaction force is at a maximum; and
      control a stiffness of the actuator so as to increase a stiffness of only the actuator positioned between the apex and the maximum reaction force position.

2. The flexible tube insertion apparatus according to claim 1, wherein the processor is further configured to specify the apex of the detected bent shape.

3. The flexible tube insertion apparatus according to claim 1, further comprising force sensors provided in the insertion section along a longitudinal axis direction of the insertion section,
   wherein the processor is configured to obtain the distribution of values of the reaction force from the force sensors.

4. The flexible tube insertion apparatus according to claim 1, wherein the processor is configured to acquire a shape of the insertion section and a current stiffness value of the actuator, and to calculate the distribution of values of the reaction force based on the shape and the current stiffness value acquired.

5. The flexible tube insertion apparatus according to claim 1, wherein when increasing the stiffness of the actuator, the processor controls the stiffness of the actuator so as to maintain a state in which a region between the apex and the maximum reaction force position is bent.

6. The flexible tube insertion apparatus according to claim 1, comprising actuators provided along a longitudinal direction of the insertion section, the actuators including the actuator recited in claim 1,
   wherein the processor is configured to control a stiffness of the actuators so that a stiffness of the actuator positioned between the apex and the maximum reaction force position among the actuators increases.

7. The flexible tube insertion apparatus according to claim 2, wherein the apex is any one of a flexure point of the insertion section, a predetermined range including the flexure point, a point at which a value of a bending radius is at a minimum in the bent shape of the insertion section, and a predetermined range including the point at which a value of a bending radius is at a minimum.

8. The flexible tube insertion apparatus according to claim 1, wherein the processor is configured to
   determine whether or not the insertion section has advanced after the stiffness of the actuator is increased, and
   when it is determined that the insertion section has advanced, decrease the stiffness of the actuator whose stiffness has been increased.

9. The flexible tube insertion apparatus according to claim 8, wherein:
   the shape detection sensor is configured to detect a change in the bent shape of the insertion section after the stiffness of the actuator is increased; and
   the processor is configured to determine, based on the change in the bent shape, whether or not the insertion section has advanced after the stiffness of the actuator is increased.

* * * * *